(12) United States Patent
Kassab et al.

(10) Patent No.: US 9,283,098 B2
(45) Date of Patent: *Mar. 15, 2016

(54) ENDOPROSTHESIS ASSEMBLIES AND METHODS TO USE THE SAME

(71) Applicant: CVDevices, LLC., San Diego, CA (US)

(72) Inventors: Ghassan S. Kassab, Zionsville, IN (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/258,881

(22) Filed: Apr. 22, 2014

(65) Prior Publication Data

US 2014/0228936 A1 Aug. 14, 2014

Related U.S. Application Data

(63) Continuation of application No. 13/151,774, filed on Jun. 2, 2011, now Pat. No. 8,702,789, which is a continuation-in-part of application No. 12/701,340, filed on Feb. 5, 2010, now Pat. No. 9,050,091, which is a continuation-in-part of application No. 11/997,147, filed as application No. PCT/US2006/029424 on Jul. 28, 2006, now Pat. No. 8,398,703.

(60) Provisional application No. 60/703,421, filed on Jul. 29, 2005.

(51) Int. Cl.
*A61F 2/06* (2013.01)
*A61F 2/82* (2013.01)
(Continued)

(52) U.S. Cl.
CPC .............. *A61F 2/82* (2013.01); *A61B 17/12022* (2013.01); *A61B 17/12113* (2013.01); *A61B 17/12118* (2013.01); *A61B 17/12186* (2013.01); *A61B 17/12195* (2013.01); *A61F 2/07* (2013.01); *A61B 17/00491* (2013.01); *A61B 2017/00561* (2013.01); *A61B 2017/00876* (2013.01); *A61B 2017/00898* (2013.01); *A61B 2019/464* (2013.01); *A61F 2/88* (2013.01); *A61F2/89* (2013.01); *A61F 2002/075* (2013.01); *A61F 2002/077* (2013.01); *A61F 2002/823* (2013.01)

(58) Field of Classification Search
CPC .................. A61B 17/12113; A61B 17/00491; A61B 17/12022; A61B 17/12186; A61B 17/12118; A61B 17/12195; A61F 2/07; A61F 2002/075
USPC .......................... 606/108, 192, 194, 195, 200; 623/1.11–1.13, 1.15, 1.42–1.45
See application file for complete search history.

(56) References Cited

U.S. PATENT DOCUMENTS 5,316,023 A * 5/1994 Palmaz et al. ................. 128/898
6,143,015 A * 11/2000 Nobles ........................... 606/194
(Continued)

*Primary Examiner* — Ashley Fishback
(74) *Attorney, Agent, or Firm* — Reichel Stohry LLP; Mark C. Reichel; Natalie J. Dean

(57) ABSTRACT

Endoprosthesis assemblies and methods for using the same. In at least one embodiment, the endoprosthesis assembly comprises an endoprosthesis comprising an impermeable inner wall defining an endoprosthesis lumen sized and shaped to permit fluid to flow therethrough, a distal balloon positioned at or near a distal end of the endoprosthesis and capable of inflation to anchor the distal end of the endoprosthesis within a luminal organ, and a proximal balloon positioned at or near a proximal end of the endoprosthesis and capable of inflation to anchor the proximal end of the endoprosthesis within the luminal organ, wherein when the endoprosthesis assembly is positioned within the luminal organ at or near an aneurysm sac, inflation of the distal balloon and the proximal balloon effectively isolates the aneurysm sac and prevents fluid within the aneurysm sac from flowing past the distal balloon and the proximal balloon.

20 Claims, 24 Drawing Sheets

(51) Int. Cl.
*A61B 17/12* (2006.01)
*A61F 2/07* (2013.01)
*A61B 17/00* (2006.01)
*A61B 19/00* (2006.01)
*A61F 2/88* (2006.01)
*A61F 2/89* (2013.01)

(56) References Cited

U.S. PATENT DOCUMENTS 6,676,694 B1 * 1/2004 Weiss ............................ 623/1.11
2006/0041281 A1 * 2/2006 Von Arx et al. ................. 607/18

* cited by examiner

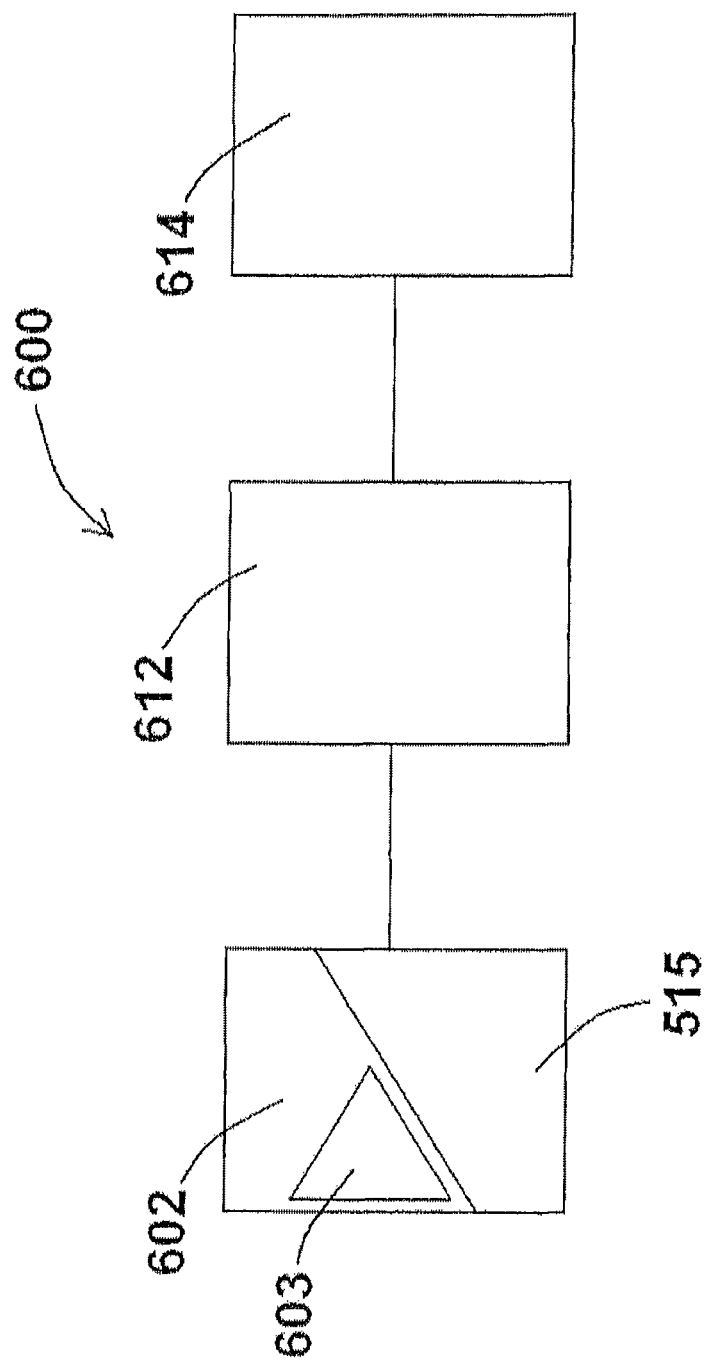

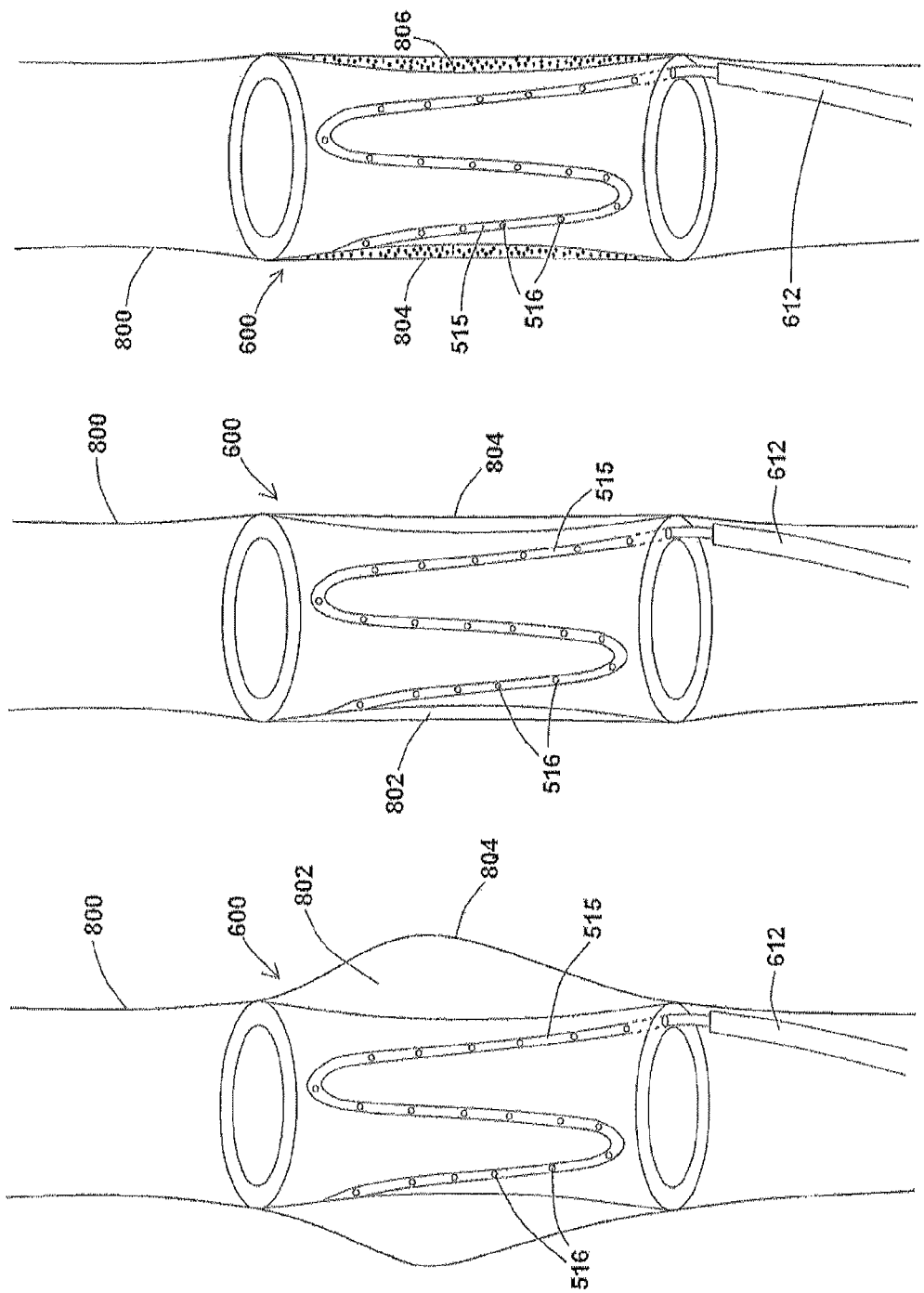

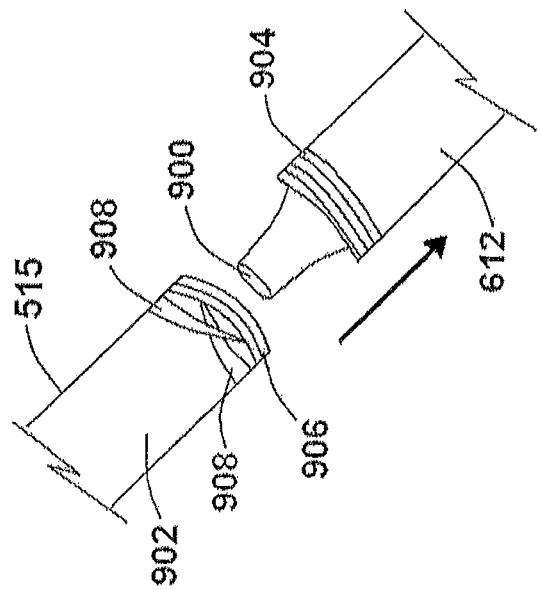
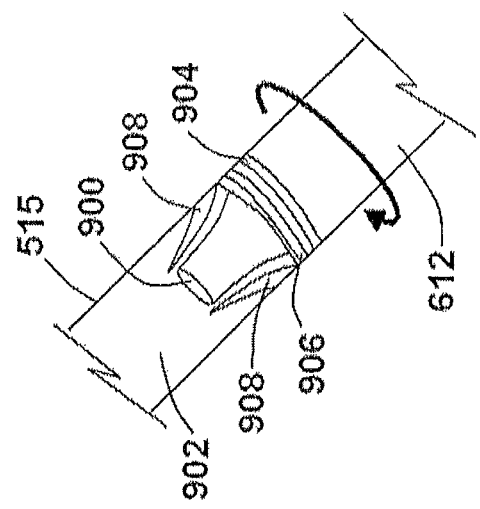
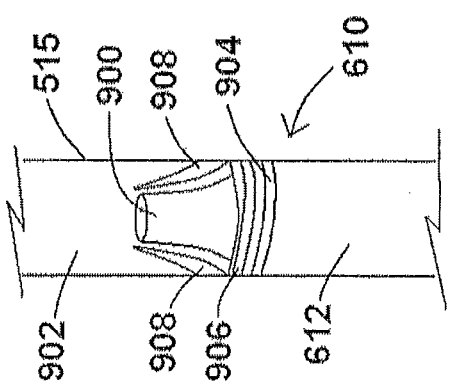

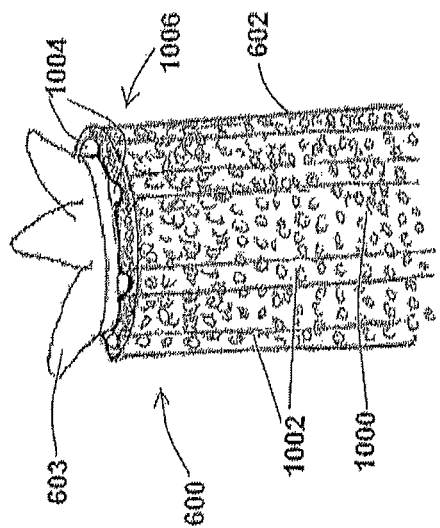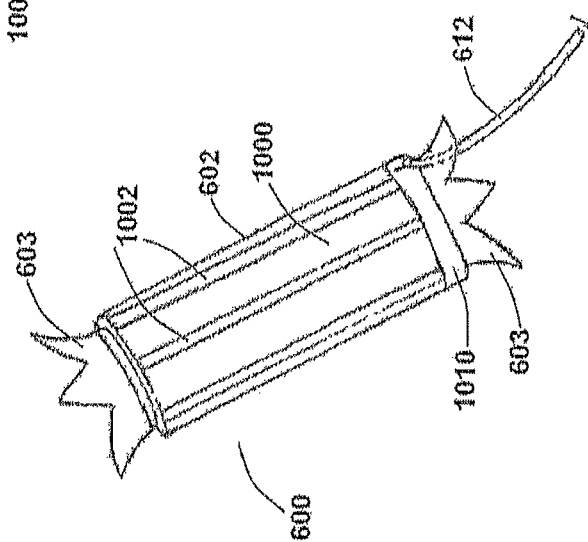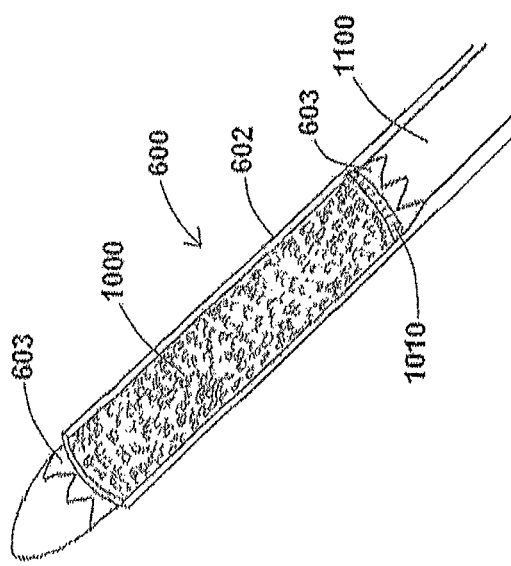

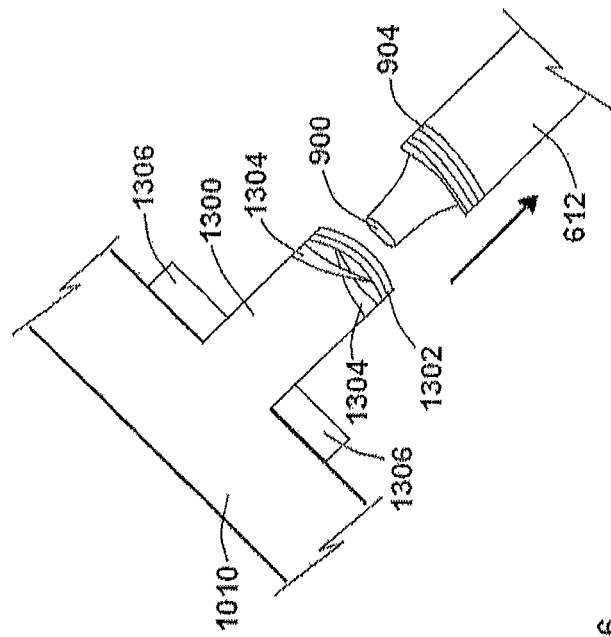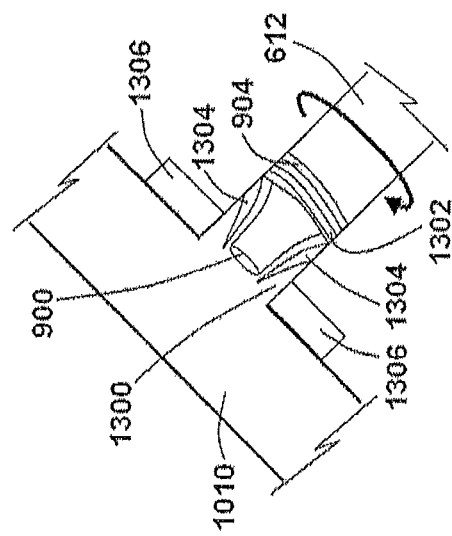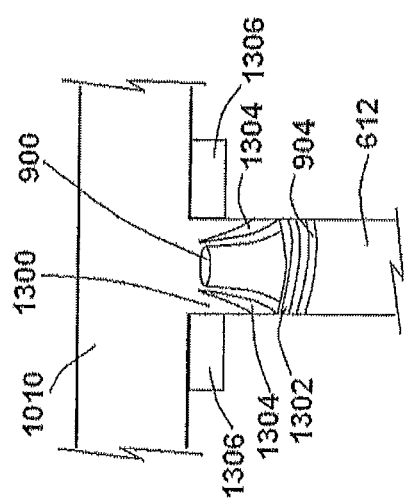

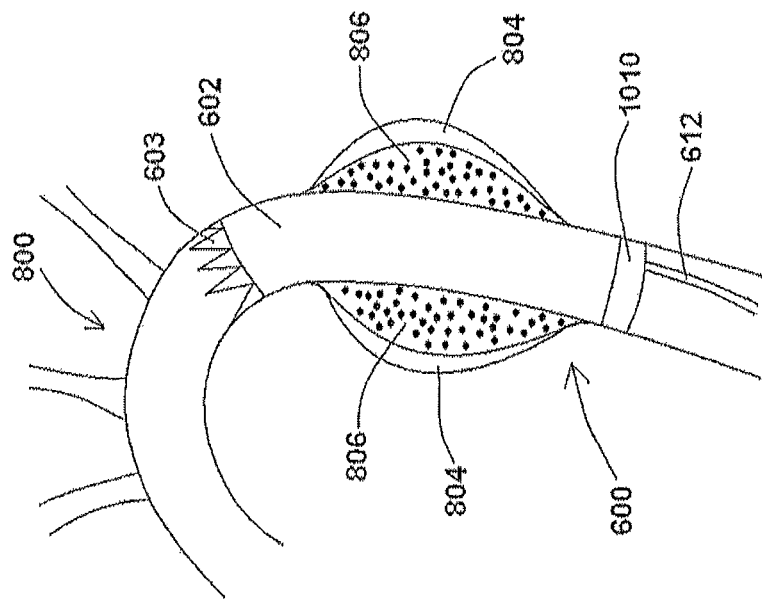
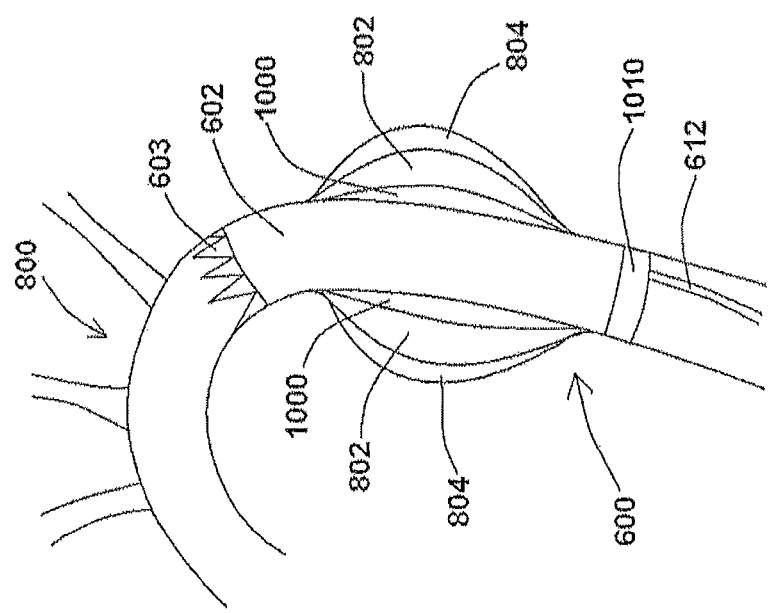
Fig. 15A
Fig. 15B

ENDOPROSTHESIS ASSEMBLIES AND METHODS TO USE THE SAME

PRIORITY

The present application is related to, claims the priority benefit of, and is a U.S. continuation patent application of, U.S. patent application Ser. No. 13/151,774, filed on Jun. 2, 2011 and issued as U.S. Pat. No. 8,702,789 on Apr. 22, 2014, which is related to, claims the priority benefit of, and is a U.S. continuation-in-part patent application of, U.S. patent application Ser. No. 12/701,340, filed Feb. 5, 2010, which is related to, claims the priority benefit of, and is a U.S. continuation-in-part patent application of, U.S. patent application Ser. No. 11/997,147, filed Jun. 30, 2008 and issued as U.S. Pat. No. 8,398,703 on Mar. 19, 2013, which is related to, claims the priority benefit of, and is a U.S. national stage entry of, International Patent Application Serial No. PCT/US2006/029424, filed Jul. 28, 2006, which is related to, and claims the priority benefit of, U.S. Provisional Patent Application Ser. No. 60/703,421, filed Jul. 29, 2005. The contents of each of these applications and patents are hereby incorporated by reference in their entirety into this disclosure.

BACKGROUND

The present disclosure relates generally to tissue support, including devices and methods for aortic tissue support and for the treatment of aneurysms.

Aortic aneurysms are formed in a vessel when the wall of the vessel weakens, either due to disease, aging, heredity or some other process. The pressure of the blood flowing through the weakened area causes the vessel wall to balloon out, forming a blood-filled aneurysm sack. Although most aneurysms begin small, they tend to enlarge over time and the risk of the sack rupturing increases as the aneurysms grows larger. Acute rupture of the aortic aneurysm is a life-threatening event, due to massive internal bleeding with a mortality rate of 75-80%. According to the Society of Vascular Surgeons, ruptured aneurysms account for more than 15,000 deaths in the U.S. each year, making the abdominal aortic aneurysm (AAA) the 13th leading cause of death in the USA. Clearly, early detection and rupture prevention is the key to the final outcome in abdominal aortic aneurysm patient. However, the condition is under-diagnosed because most patients with AAA are asymptomatic. Consequently, the majority of the anomalies are discovered unexpectedly during routine tests or procedures. An estimated 1.7 million Americans have AAA, but only about 250,000-300,000 patients are diagnosed every year.

There is no proven medical treatment for AAA, and surgical repair has been the only common therapeutic option. A standard open repair has been associated with significant morbidity and mortality, prolonged recovery, and late complications. Because of these limitations, many patients and their physicians choose to defer operative treatment. Recently, endovascular aneurysm repair (EVAR) has become an alternative and some studies favorably compare endovascular repair with a standard open repair. However, significant concern exists relating to endovascular repair and its value is a subject of healthy debate. Endovascular abdominal aortic aneurysm repair has gained acceptance as a minimally invasive alternative to open surgery in selected patients. While long-term durability remains uncertain, patients and their physicians are willing to accept a degree of uncertainty in exchange for dramatic reduction in duration of hospital stay, and need for blood transfusion. Hence, improvements in the current EVAR devices can potentially make this approach standard for AAA repair.

Most patients diagnosed with AAA are not considered for surgery or endovascular repair unless the aneurysm is at least 5 cm in diameter, the point at which the risk of rupture clearly exceeds the risk of repair. Those with a smaller aneurysm are followed closely with regular imaging studies. There has been much speculation over the years about the preventive use of endovascular aneurysm repair in patients with aneurysms smaller than 5 cm, however, vascular surgeons so far have been reluctant to use EVAR for smaller aneurysms due to the concern about the long term durability of the technology and the lack of data demonstrating a clear benefit of early intervention. Moreover, although EVAR outcomes have improved over the years as physicians gain more experience with the procedure, it remains a technically demanding procedure that requires extensive training and this has limited the number of physicians qualified to perform EVAR.

Despite the shortcoming relating to training, a number of endovascular devices have been evaluated in clinical trials designed to gain approval from governmental agencies. These devices differ with respect to design features, including modularity, metallic composition and the structure of the stent, thickness, porosity, chemical composition of the polymeric fabric, methods for attaching the fabric to the stent, and presence or absence of an active method of fixing the device to the aortic wall with bars or hooks. With consideration of the numbers of structural variations between different brands of endovascular devices, it would be remarkable if clinical outcome were not equally dissimilar. Parameters such as frequency of endoleak, long-term change in size of the aneurysm sac, reason for device migration and limb thrombosis may be linked to specific device design features. Hence, any improvements in the deployment and attachment of stent graft would increase the utility of EVAR.

Important drivers and limiters of EVAR are playing a big role in the decision of the treatment. The drivers include: 1) Less invasive compared to open repair, which translates into shorter hospitalization and recovery and lower major morbidity; 2) Aging of the population will increase the incidence and prevalence of AAA and thoracic aortic aneurysm (TAA); 3) Increasingly informed patient population will generate strong patient demand for minimally invasive therapy, and 4) Next-generation devices, expected to address wider patient population (including those with thoracic disease) and reduce complications relative to current model. The limiters, on the other hand, include the following: 1) Clinical literature does not support prophylactic endovascular treatment of the small aneurysm with a low risk of fracture; 2) High rate of late complication necessitates extensive and potentially life-long post procedural follow-up (not required for open repair) and repeat intervention that makes endovascular therapy potentially more costly than open surgery; 3) Current device is not applicable to full-range of AMA patients; 4) Technical demands of the approach require devices and time-consuming training that may eliminate rapid adoption of new products, particularly for a specialist with a smaller case load, and 5) Surgical conversion is complicated by the presence of the stent graft. Improvements in the current devices would certainly make the drivers outweigh the limiters.

The most important trial conducted to date is the EVAR 1 study, which randomized over 1,000 elective patients with aneurysms 5.5 cm or larger comparing EVAR to open surgical repair. Thirty-day mortality published this year demonstrated a clear advantage of EVAR (1.6% vs. 4.7% for open repair). However, EVAR patients had significantly higher rates of secondary intervention (9.8% vs. 5.8%). A second version study, EVAR 2, is comparing EVAR with best medical treatment in patients unsuitable for surgical repair. The 12-month result for EVAR 1 are particularly important, as physicians will be looking to see if endovascular therapy is able, for the first time, to demonstrate significant survival benefit over open surgery after one year.

Despite some of its inherent drawbacks, EVAR is expected to experience robust growth over the next several years. The U.S. AAA graft market is projected to increase from $288 M in 2004 to $552 M in 2008. In addition, contribution from thoracic graft systems, beginning this year, will grow the total US aortic stent market to over $670 M in 2008 (Endovascular, 2005).

Ongoing areas of concern with endovascular abdominal aortic repair are; 1) Rate of late complications; 2) Appreciable intervention and conversion rates; 3) Dubious cost advantage compared to open surgery due to the need of intervention and regular patient monitoring; 4) Increased device failure with time; 5) Increased procedural failure with time, and 6) Rupture risk of 1% per year after endovascular repair is not dramatically different from the natural history of small 5 cm aneurysms. Hence, there is high rate of secondary intervention (primarily to treat endoleaks—persistent flow within the aneurysm sac that in certain cases can lead to aneurysm rupture, if left untreated), and increasing rate of device failures over time. In addition to endoleaks, other late complications in AAA graft trials include device migration, modular component separation, graft thrombosis, bar separation, and material fatigue.

Currently in the U.S., about 60,000 abdominal aortic aneurysm (AAA) patients require intervention each year. The majority of the patients are treated with open surgical repair, while about 40% are treated with EVAR. Although open AAA repair is highly successful, it is also extremely invasive, with an operative mortality rate between 5-10%. Thus, patients with significant co-morbidities are generally not candidates for open repair. These patients are the primary beneficiaries of endovascular grafting or EVAR. EVAR gained tremendous popularity in 1990 after commercial AAA stent graft became available in the U.S. After a one-year period of adjustment, however, problems with the first generation device began to surface including migration, endoleak and endotension. Although physicians remain confident, they have for the most part recovered from the disappointment associated with the first generation technology and are looking forward to future advances in the field. Further expansion of endovascular repair is required to improve the device and good long-term results from large randomized trials comparing EVAR with open surgery. There is no doubt that a device that overcomes some of the current shortcomings of EVAR devices such as migration, endoleak and endotension is greatly welcomed for the treatment of aortic aneurysm.

Thus, a need exists in the art for an alternative to the conventional methods of aneurysm treatment. A further need exist for a reliable, accurate and minimally invasive device or technique of treating aneurysms and minimizing their risks of enlarging or rupturing.

BRIEF SUMMARY

The current EVAR devices and methods are inadequate. They are prone to such fatal problems as migration, endoleak, and endotension. In order to address this medical problem, the present disclosure provides devices and methods for minimizing and/or preventing the growth or rupture of aneurysms or other vascular growth through the use of magnetic tissue support.

In at least one embodiment of an endograft assembly of the present disclosure, the endograft assembly comprises an endograft having an inner wall, an outer wall, and a graft structure positioned between the inner wall and the outer wall, the inner wall of the endograft defining an endograft lumen sized and shaped to permit fluid to flow therethrough, and a tube defining one or more tube openings, said tube coupled to the endograft in a configuration whereby the one or more tube openings are exposed along the outer wall of the endograft. In another embodiment, the tube is coupled to the outer wall of the endograft. In yet another embodiment, the tube is coupled to the endograft between the inner wall and the outer wall of the endograft. In an additional embodiment, the endograft further comprises a length, and wherein the tube extends substantially the length of the endograft.

In at least one embodiment of an endograft assembly of the present disclosure, the inner wall of the endograft is impermeable to fluids, and wherein the outer wall of the endograft is permeable to fluids. In another embodiment, the endograft assembly further comprises a catheter having a distal catheter end, a proximal catheter end, and defining a lumen therethrough, wherein the distal catheter end of the catheter is configured to be removably coupled to a proximal tube end of the tube. In an additional embodiment, the endograft assembly further comprises a suction/infusion source configured to be coupled to the catheter at or near the proximal catheter end, the suction/infusion source capable of providing suction within the lumen of the catheter and further capable of injecting a substance into the lumen of the catheter. In yet an additional embodiment, the endograft assembly further comprises a suction/infusion source configured to be coupled to the catheter at or near the proximal catheter end, the suction/infusion source capable of providing suction within the lumen of the catheter to facilitate removal of blood present within an aneurysm sac when the endograft assembly is positioned within a vessel at or near the site of a vessel aneurysm and when the catheter is coupled to the tube.

In at least one embodiment of an endograft assembly of the present disclosure, the endograft assembly further comprises a suction/infusion source configured to be coupled to the catheter at or near the proximal catheter end, the suction/infusion source capable of injecting a substance into the lumen of the catheter and into an aneurysm sac when the endograft assembly is positioned within a vessel at or near the site of a vessel aneurysm and when the catheter is coupled to the tube. In another embodiment, the substance is capable of forming a cast within the aneurysm sac when it is injected to the aneurysm sac, said cast providing structural reinforcement to the vessel aneurysm. In yet another embodiment, the substance is selected from the group consisting of ethylene vinyl alcohol copolymer, acetate polymer, ethylene vinyl alcohol dissolved in dimethyl sulfoxide, cellulose, cyanoacrylate, glue, and gel magnetic polymer.

In at least one embodiment of an endograft assembly of the present disclosure, the endograft comprises a configuration selected from the group consisting of a straight configuration and a curved configuration. In an additional embodiment, wherein the tube comprises a proximal tube end and a distal tube end, and wherein the proximal tube end comprises a tube threaded portion. In yet an additional embodiment, the tube threaded portion corresponds to a catheter threaded portion located at a distal catheter end of a catheter, permitting the catheter to be rotatably coupled to the tube. In another embodiment, the catheter further comprises a catheter tip at the distal catheter end, the catheter tip configured to fit within a lumen of the tube. In at least one embodiment of an endograft assembly of the present disclosure, the tube comprises a proximal tube end and a distal tube end, and wherein the proximal tube end comprises one or more unidirectional valves. In another embodiment, the one or more unidirectional valves permit fluid to flow out of the tube when a catheter is coupled thereto, and wherein the one or more unidirectional valves prevents fluid from flowing out of the tube when the catheter is not coupled thereto. In yet another embodiment, the endograft assembly comprises one or more materials selected from the group consisting of nitinol, plastic, polyurethane, silastic, polyvinylchloride, and polytetrafluoroethylene.

In at least one embodiment of an endograft assembly of the present disclosure, the graft structure of the endograft assembly is capable of a first, collapsed configuration, and is further capable of a second, expanded configuration. In an additional embodiment, the graft structure is selected from the group consisting of a traditional stent, a balloon-expandable device, or an autoexpandable device. In yet an additional embodiment, the inner wall comprises a fluid-impermeable fabric, and wherein the outer wall comprises a fluid-permeable fabric. In another embodiment, the endograft assembly further comprises a sponge sheath having a distal end and a proximal end, the sponge sheath coupled to the outer wall of the endograft and configured to permit blood flow therethrough. In yet another embodiment, the sponge sheath defines one or more sponge channels therein, said sponge channels configured to permit fluid flow therethrough.

In at least one embodiment of an endograft assembly of the present disclosure, the endograft assembly comprises an endograft having an inner wall and an outer wall, and a graft structure positioned between the inner wall and the outer wall, the inner wall of the endograft defining an endograft lumen sized and shaped to permit fluid to flow therethrough, a tube comprising a proximal tube end, a distal tube end, one or more unidirectional valves at or near the proximal tube end, and one or more tube openings defined along the tube, said tube coupled to the endograft in a configuration whereby the one or more tube openings are exposed along the outer wall of the endograft, a catheter having a distal catheter end, a proximal catheter end, and defining a lumen therethrough, wherein the distal catheter end of the catheter is configured to be removably coupled to a proximal tube end of the tube, and a suction/infusion source configured to be coupled to the catheter at or near the proximal catheter end, the suction/infusion source capable of providing suction within the lumen of the catheter and further capable of injecting a substance into the lumen of the catheter In at least one embodiment of method for using an endograft assembly of the present disclosure, the method comprising the steps of delivering an endograft assembly within a vessel of a patient at or near the site of a vessel aneurysm, the endograft assembly comprising an endograft, a tube coupled to the endograft, the tube defining one or more tube openings, a catheter removably coupled to the tube, and a suction/infusion source coupled to the catheter, operating a suction/infusion source to remove blood present within an aneurysm sac of the vessel aneurysm, and operating the suction/infusion source to inject a substance into the aneurysm sac to form a cast at or near the site of the vessel aneurysm. In another embodiment, the step of delivering the endograft assembly further comprises the step of deploying the endograft assembly within the vessel. In yet another embodiment, the step of operating a suction/infusion source to remove blood present within an aneurysm sac causes a wall of the vessel aneurysm to collapse toward the endograft assembly. In an additional embodiment, the substance is capable of forming a cast within the aneurysm sac when it is injected to the aneurysm sac, said cast providing structural reinforcement to the vessel aneurysm.

In at least one embodiment of an endograft assembly of the present disclosure, the endograft assembly comprises an endograft having an inner wall and an outer wall, and a graft structure positioned between the inner wall and the outer wall, the inner wall of the endograft defining an endograft lumen sized and shaped to permit fluid to flow therethrough, and a sponge sheath having a distal end and a proximal end, the sponge sheath coupled to the outer wall of the endograft and configured to permit blood flow therethrough. In another embodiment, the inner wall of the endograft is impermeable to fluids, and wherein the outer wall of the endograft is permeable to fluids. In yet another embodiment, the sponge sheath defines one or more sponge channels therein, said sponge channels configured to permit fluid flow therethrough.

In at least one embodiment of an endograft assembly of the present disclosure, the endograft assembly further comprises a reservoir bag coupled to the sponge sheath at or near the proximal end of the sponge sheath, said reservoir bag capable of receiving fluid from the sponge sheath and the one or more sponge channels. In another embodiment, the endograft assembly further comprises a catheter having a distal catheter end, a proximal catheter end, and defining a lumen therethrough, wherein the distal catheter end of the catheter is configured to be removably coupled to the reservoir bag. In yet another embodiment, the endograft assembly further comprises a suction/infusion source configured to be coupled to the catheter at or near the proximal catheter end, the suction/infusion source capable of providing suction within the lumen of the catheter and further capable of injecting a substance into the lumen of the catheter. In an additional embodiment, the endograft assembly further comprises a suction/infusion source configured to be coupled to the catheter at or near the proximal catheter end, the suction/infusion source capable of providing suction within the lumen of the catheter to facilitate removal of blood present within an aneurysm sac when the endograft assembly is positioned within a vessel at or near the site of a vessel aneurysm and when the catheter is coupled to the reservoir bag.

In at least one embodiment of an endograft assembly of the present disclosure, the endograft assembly further comprises a suction/infusion source configured to be coupled to the catheter at or near the proximal catheter end, the suction/infusion source capable of injecting a substance into the lumen of the catheter and into an aneurysm sac when the endograft assembly is positioned within a vessel at or near the site of a vessel aneurysm and when the catheter is coupled to the reservoir bag. In another embodiment, the substance is capable of forming a cast within the aneurysm sac when it is injected to the aneurysm sac, said cast providing structural reinforcement to the vessel aneurysm. In yet another embodiment, the substance is selected from the group consisting of ethylene vinyl alcohol copolymer, acetate polymer, ethylene vinyl alcohol dissolved in dimethyl sulfoxide, cellulose, cyanoacrylate, glue, and gel magnetic polymer.

In at least one embodiment of an endograft assembly of the present disclosure, the endograft comprises a configuration selected from the group consisting of a straight configuration and a curved configuration. In another embodiment, the reservoir bag comprises a reservoir bag threaded portion. In yet another embodiment, the reservoir bag threaded portion corresponds to a catheter threaded portion located at a distal catheter end of a catheter, permitting the catheter to be rotatably coupled to the reservoir bag. In an additional embodiment, the catheter further comprises a catheter tip at the distal catheter end, the catheter tip configured to fit within a lumen of the reservoir bag.

In at least one embodiment of an endograft assembly of the present disclosure, the reservoir bag comprises one or more unidirectional valves. In an additional embodiment, the one or more unidirectional valves permit fluid to flow out of the reservoir bag when a catheter is coupled thereto, and wherein the one or more unidirectional valves prevents fluid from flowing out of the reservoir bag when the catheter is not coupled thereto. In yet an additional embodiment, the endograft assembly comprises one or more materials selected from the group consisting of plastic, polyurethane, silastic, polyvinylchloride, and polytetrafluoroethylene. In another embodiment, the endograft assembly is capable of a first, collapsed configuration, and wherein the endograft assembly is capable of a second, expanded configuration. In yet another embodiment, the sponge sheath comprises one or more materials selected from the group consisting of cellulose fiber, wood fiber, foamed plastic polymer, polyurethane, silastic, rubber, polytetrafluoroethylene, synthetic sponge, natural sponge, low-density polyether, polyvinyl alcohol, and polyester.

In at least one embodiment of an endograft assembly of the present disclosure, the endograft assembly comprises an endograft having an inner wall and an outer wall, and a graft structure positioned between the inner wall and the outer wall, the inner wall of the endograft defining an endograft lumen sized and shaped to permit fluid to flow therethrough, a sponge sheath having a distal end and a proximal end, the sponge sheath coupled to the outer wall of the endograft and configured to permit blood flow therethrough, the sponge sheath defining one or more sponge channels configured to permit fluid flow therethrough, a reservoir bag coupled to the sponge sheath at or near the proximal end of the sponge sheath, said reservoir bag capable of receiving fluid from the sponge sheath and the one or more sponge channels, a catheter having a distal catheter end, a proximal catheter end, and defining a lumen therethrough, wherein the distal catheter end of the catheter is configured to be removably coupled to the reservoir bag, and a suction/infusion source configured to be coupled to the catheter at or near the proximal catheter end, the suction/infusion source capable of providing suction within the lumen of the catheter and further capable of injecting a substance into the lumen of the catheter.

In at least one embodiment of a method for using an endograft assembly of the present disclosure, the method comprises the steps of delivering an endograft assembly within a vessel of a patient at or near the site of a vessel aneurysm, the endograft assembly comprising an endograft, a sponge sheath coupled to the endograft, the sponge sheath defining one or more sponge channels, a reservoir bag coupled to the sponge sheath, said reservoir bag capable of receiving fluid from the sponge sheath and the one or more sponge channels, a catheter removably coupled to the reservoir bag, and a suction/infusion source coupled to the catheter, operating a suction/infusion source to remove blood present within an aneurysm sac of the vessel aneurysm, and operating the suction/infusion source to inject a substance into the aneurysm sac to form a cast at or near the site of the vessel aneurysm. In another embodiment, the step of delivering the endograft assembly further comprises the step of deploying the endograft assembly within the vessel. In yet another embodiment, the step of operating a suction/infusion source to remove blood present within an aneurysm sac causes a wall of the vessel aneurysm to collapse toward the endograft assembly. In an additional embodiment, the substance is capable of forming a cast within the aneurysm sac when it is injected to the aneurysm sac, said cast providing structural reinforcement to the vessel aneurysm.

In at least one embodiment of an endoprosthesis assembly of the present disclosure, the endoprosthesis assembly comprises an endoprosthesis comprising an impermeable inner wall defining an endoprosthesis lumen sized and shaped to permit fluid to flow therethrough, a distal balloon positioned at or near a distal end of the endoprosthesis, the distal balloon capable of inflation to anchor the distal end of the endoprosthesis within a luminal organ, and a proximal balloon positioned at or near a proximal end of the endoprosthesis, the proximal balloon capable of inflation to anchor the proximal end of the endoprosthesis within the luminal organ, wherein when the endoprosthesis assembly is positioned within the luminal organ at or near an aneurysm sac, inflation of the distal balloon and the proximal balloon effectively isolates the aneurysm sac and prevents fluid within the aneurysm sac from flowing past the distal balloon and the proximal balloon and into other areas of vasculature adjacent to the aneurysm sac. In another embodiment, the endoprosthesis assembly further comprises a first tube defining one or more first tube openings, the first tube coupled to an outside of the inner wall of the endoprosthesis in a first configuration whereby the one or more first tube openings are exposed along the outside of the inner wall of the endoprosthesis.

In at least one embodiment of an endoprosthesis assembly of the present disclosure, the endoprosthesis further comprises an outer wall adjacent to the inner wall, the outer wall configured to permit fluid to flow therethrough. In an additional embodiment, the endoprosthesis assembly further comprises a first tube defining one or more first tube openings, the first tube positioned within the outer wall of the endoprosthesis in a first configuration whereby the one or more first tube openings are exposed within the outer wall of the endoprosthesis. In yet an additional embodiment, the endoprosthesis assembly further comprises a first tube defining one or more first tube openings, the first tube positioned adjacent to the outer wall of the endoprosthesis in a first configuration whereby the one or more first tube openings are exposed along the outer wall of the endoprosthesis. In another embodiment, the endoprosthesis assembly further comprises a first tube defining one or more first tube openings, the first tube positioned at or within the outer wall of the endoprosthesis in a first configuration whereby the one or more first tube openings are exposed at or near the outer wall of the endoprosthesis, and a second tube defining one or more second tube openings, the second tube positioned at or within the outer wall of the endoprosthesis in a second configuration whereby the one or more second tube openings are exposed at or near the outer wall of the endoprosthesis. In yet another embodiment, the first configuration is a relative "S" configuration along at least half of a distance between the distal end and the proximal end of the endoprosthesis, and wherein the second configuration is a circumferential configuration at or near the distal end of the endoprosthesis.

In at least one embodiment of an endoprosthesis assembly of the present disclosure, the endoprosthesis assembly further comprises a graft structure positioned adjacent to the inner wall of the endoprosthesis, the graft structure capable of expansion to expand the endoprosthesis. In another embodiment, the endoprosthesis assembly further comprises a catheter having a distal catheter end, a proximal catheter end, and defining a suction/infusion lumen therethrough and an inflation/deflation lumen therethrough, wherein the distal catheter end of the catheter is configured to be removably coupled to the endoprosthesis at or near the proximal end of the endoprosthesis. In yet another embodiment, the endoprosthesis assembly further comprises a suction/infusion source configured to be coupled to the catheter at or near a proximal catheter end, the suction/infusion source capable of providing suction within the suction/infusion lumen of the catheter and further capable of injecting a substance into the suction/infusion lumen of the catheter. In an additional embodiment, the substance is capable of forming a cast within the aneurysm sac when it is injected to the aneurysm sac, said cast providing structural reinforcement to a vessel wall surrounding the aneurysm sac. In yet an additional embodiment, the endoprosthesis assembly further comprises a suction/infusion source configured to be coupled to the catheter at or near a proximal catheter end, the suction/infusion source capable of providing suction within the suction/infusion lumen of the catheter to facilitate removal of blood present within the aneurysm sac when the endoprosthesis assembly is positioned within the luminal organ at or near the aneurysm sac and when the catheter is coupled to the endoprosthesis.

In at least one embodiment of an endoprosthesis assembly of the present disclosure, the endoprosthesis assembly further comprises a valve mechanism coupled to the endoprosthesis, the valve mechanism configured to receive a distal catheter end of a catheter, the valve mechanism further configured to permit fluid to flow in and out of the valve mechanism when the catheter is coupled thereto, the valve mechanism further configured to prevent fluid from flowing in and out of the valve mechanism when the catheter is not coupled thereto. In an additional embodiment, the endoprosthesis assembly further comprises a magnetic mechanism coupled to the endoprosthesis assembly at or near the distal end of the endoprosthesis, the magnetic mechanism configured to attract a second magnetic mechanism of a second endoprosthesis assembly positioned relative to the endoprosthesis assembly. In yet an additional embodiment, the distal balloon has a configuration selected from the group consisting of a 360° configuration around the endoprosthesis, about a 180° configuration around the endoprosthesis, about a 270° configuration around the endoprosthesis, and a configuration between about 180° and about 360° around the endoprosthesis. In another embodiment, the one or more first tube openings are positioned about approximately half of a relative side of the endoprosthesis. In yet another embodiment, the endoprosthesis assembly further comprises a pressure sensor coupled thereto, the pressure sensor operable to obtain at least one pressure measurement of an environment surrounding the endoprosthesis.

In at least one embodiment of an endoprosthesis assembly of the present disclosure, the endoprosthesis assembly further comprises a second endoprosthesis comprising a second impermeable inner wall defining a second endoprosthesis lumen sized and shaped to permit fluid to flow therethrough, a second distal balloon positioned at or near a second distal end of the second endoprosthesis, the second distal balloon capable of inflation to anchor the second distal end of the second endoprosthesis within the luminal organ, and a second proximal balloon positioned at or near a second proximal end of the second endoprosthesis, the second proximal balloon capable of inflation to anchor the second proximal end of the second endoprosthesis within the second luminal organ, wherein when the distal end of the endoprosthesis is positioned distal to the aneurysm sac of the luminal organ, the proximal end of the endoprosthesis is configured to be positioned within a first luminal organ bifurcation of the luminal organ, wherein when the second distal end of the second endoprosthesis is positioned distal to the aneurysm sac of the luminal organ, the second proximal end of the second endoprosthesis is configured to be positioned within a second luminal organ bifurcation of the luminal organ, and wherein inflation of the distal balloon, the second distal balloon, the proximal balloon, and the second proximal balloon effectively isolates the aneurysm sac distal to the aneurysm sac within an unbifurcated portion of the luminal organ and proximal to the aneurysm sac within the first luminal organ bifurcation and the second luminal organ bifurcation. In another embodiment, the endoprosthesis assembly further comprises a first magnetic mechanism coupled to the endoprosthesis assembly at or near the distal end of the endoprosthesis, and a second magnetic mechanism coupled to the second endoprosthesis assembly at or near the second distal end of the second endoprosthesis, wherein the first magnetic mechanism and the second magnetic mechanism are configured to attract one another when positioned relative to one another.

In at least one embodiment of an endoprosthesis system of the present disclosure, the endoprosthesis system further comprises a first endoprosthesis assembly and a second endoprosthesis assembly, each of the first endoprosthesis assembly and the second endoprosthesis assembly comprising an endoprosthesis comprising an impermeable inner wall defining an endoprosthesis lumen sized and shaped to permit fluid to flow therethrough, a distal balloon positioned at or near a distal end of the endoprosthesis, the distal balloon capable of inflation to anchor the distal end of the endoprosthesis within a luminal organ, and a proximal balloon positioned at or near a proximal end of the endoprosthesis, the proximal balloon capable of inflation to anchor the proximal end of the endoprosthesis within the luminal organ, a first tube defining one or more first tube openings, the first tube positioned at or within the outer wall of the endoprosthesis in a first configuration whereby the one or more first tube openings are exposed at or near the outer wall of a relative side of the endoprosthesis, wherein when the first endoprosthesis assembly and the second endoprosthesis assembly are positioned within the luminal organ adjacent to one another at or near an aneurysm sac, inflation of each of the distal balloons and each of the proximal balloons effectively isolates the aneurysm sac and prevents fluid within the aneurysm sac from flowing past the distal balloons and the proximal balloons and into other areas of vasculature adjacent to the aneurysm sac. In another embodiment, the endoprosthesis system further comprises a first catheter and a second catheter, each of the first catheter and the second catheter having a distal catheter end, a proximal catheter end, and defining a suction/infusion lumen therethrough and an inflation/deflation lumen therethrough, wherein the distal catheter ends of the catheters are configured to be removably coupled to each individual endoprosthesis, respectively, at or near the proximal ends of each endoprosthesis. In yet another embodiment, the endoprosthesis system further comprises a first valve mechanism and a second valve mechanism, each valve mechanism coupled to each endoprosthesis, respectively, each valve mechanism configured to receive a distal catheter end of a catheter, each valve mechanism further configured to permit fluid to flow in and out of each valve mechanism when each catheter is coupled thereto, each valve mechanism further configured to prevent fluid from flowing in and out of each valve mechanism when each catheter is not coupled thereto. In an additional embodiment, the endoprosthesis system further comprises a first magnetic mechanism and a second magnetic mechanism, each magnetic mechanism coupled to each distal end of each endoprosthesis, respectively, wherein the first magnetic mechanism and the second magnetic mechanism are configured to attract one another when positioned relative to one another.

In at least one embodiment of a method for using an endoprosthesis assembly, the method comprises the steps of delivering an endoprosthesis assembly within a vessel of a patient at or near the site of a vessel aneurysm sac of a vessel aneurysm, the endoprosthesis assembly comprising an endoprosthesis comprising an impermeable inner wall defining an endoprosthesis lumen sized and shaped to permit fluid to flow therethrough, a distal balloon positioned at or near a distal end of the endoprosthesis, the distal balloon capable of inflation to anchor the distal end of the endoprosthesis within a luminal organ, a proximal balloon positioned at or near a proximal end of the endoprosthesis, the proximal balloon capable of inflation to anchor the proximal end of the endoprosthesis within the luminal organ, and a catheter having a distal catheter end, a proximal catheter end, and defining a suction/infusion lumen therethrough and an inflation/deflation lumen therethrough, wherein the distal catheter end of the catheter is configured to be removably coupled to the endoprosthesis at or near the proximal end of the endoprosthesis, operating an inflation/deflation source in communication with the inflation/deflation lumen of the catheter to inflate the distal balloon and the proximal balloon to isolate the aneurysm sac and prevent fluid within the aneurysm sac from flowing past the distal balloon and the proximal balloon and into other areas of vasculature adjacent to the aneurysm sac, operating a suction/infusion source in communication with the suction/infusion lumen of the catheter to remove blood present within the aneurysm sac, and operating the suction/infusion source to inject a substance into the aneurysm sac to form a cast at or near the vessel aneurysm. In another embodiment, the method further comprises the steps of operating the inflation/deflation source in communication with the inflation/deflation lumen of the catheter to deflate the distal balloon and the proximal balloon, disconnecting the catheter from the endoprosthesis, and removing the catheter from the patient. In yet another embodiment, the step of delivering the endoprosthesis assembly further comprises the step of deploying the endoprosthesis assembly within the vessel.

In at least one embodiment of a method for using an endoprosthesis assembly, the step of operating a suction/infusion source to remove blood present within the aneurysm sac causes a wall of the vessel aneurysm to collapse toward the endoprosthesis assembly. In another embodiment, the step of operating a suction/infusion source to remove blood is performed along with a step of obtaining a first pressure measurement using a pressure sensor in communication with the aneurysm sac so to avoid negative pressure within the aneurysm sac, and wherein the step of operating a suction/infusion source to inject a substance is performed along with a step of obtaining a second pressure measurement using the pressure sensor so to avoid excessive pressure within the aneurysm sac. In an additional embodiment, the step of delivering an endoprosthesis assembly further comprises delivering a second endoprosthesis assembly within the vessel of the patient at or near the site of the vessel aneurysm sac of the vessel aneurysm, the second endoprosthesis assembly comprising a second endoprosthesis comprising a second impermeable inner wall defining a second endoprosthesis lumen sized and shaped to permit fluid to flow therethrough, a second distal balloon positioned at or near a second distal end of the second endoprosthesis, the second distal balloon capable of inflation to anchor the second distal end of the second endoprosthesis within a luminal organ, a second proximal balloon positioned at or near a second proximal end of the second endoprosthesis, the second proximal balloon capable of inflation to anchor the second proximal end of the second endoprosthesis within the luminal organ, and a second catheter having a second distal catheter end, a second proximal catheter end, and defining a second suction/infusion lumen therethrough and a second inflation/deflation lumen therethrough, wherein the second distal catheter end of the second catheter is configured to be removably coupled to the second endoprosthesis at or near the second proximal end of the second endoprosthesis, and wherein the step of operating the inflation/deflation source is performed to also inflate the second distal balloon and the second proximal balloon to isolate the aneurysm sac and prevent fluid within the aneurysm sac from flowing past the second distal balloon and the second proximal balloon and into other areas of vasculature adjacent to the aneurysm sac. In yet an additional embodiment, the step of delivering an endoprosthesis assembly is performed to position the proximal end of the endoprosthesis within a first luminal organ bifurcation of the luminal organ and to position the second proximal end of the second endoprosthesis within a second luminal organ bifurcation of the luminal organ.

BRIEF DESCRIPTION OF THE DRAWINGS

FIG. 6E shows a block diagram of various components of an endograft assembly according to an exemplary embodiment of the present disclosure;

FIGS. 8A-8C show an endograft assembly positioned within a bodily vessel according to an exemplary embodiment of the present disclosure;

FIGS. 9A-9C show a connection and disconnection of a removable catheter and a tube of an endograft assembly according to an exemplary embodiment of the present disclosure;

FIGS. 11A-12B show portions of endograft assemblies comprising a sponge sheath according to exemplary embodiments of the present disclosure;

FIGS. 13A-13C show a connection and disconnection of a removable catheter and a reservoir bag of an endograft assembly according to an exemplary embodiment of the present disclosure;

FIGS. 15A and 15B show an endograft assembly positioned within a bodily vessel according to an exemplary embodiment of the present disclosure;

DETAILED DESCRIPTION

Figure 1:
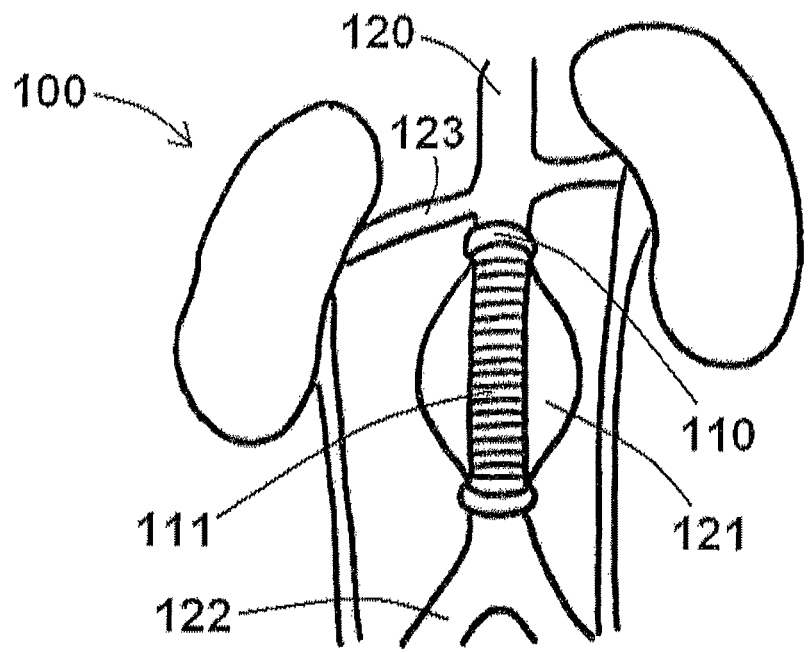
FIG. 1 shows a front view of a magnetically stabilized luminal stent graft assembly with two magnetic bodies according to an exemplary embodiment of the present disclosure.
Figure 2:
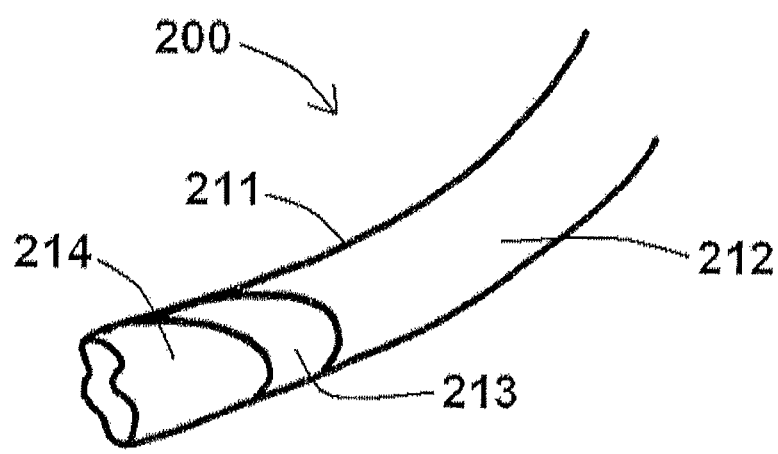
FIG. 2 shows an angled view of a luminal stent graft with a magnetic covering and powder according to an exemplary embodiment of the present disclosure.

The disclosure of the present application provides various endograft and endoprosthesis devices and methods for using the same. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As discussed briefly above, the aneurysm size appears to be the one of the most important factors determining risk of aneurysm rupture. Changes in aneurysm dimension have been used as a surrogate marker for clinical efficacy after endovascular repair. Other morphological changes, including progressive angulation, and aortic neck enlargement, may occur in response to either aneurysm exclusion or associated degenerative changes in adjacent segments, respectively. In endovascular repair, the aneurysm sac is left intact and, as a consequence, this feature plays an important role in outcome assessment, defining the success or failure of aneurysm exclusion. Long term aneurysm exclusion and device stabilization is dependent on the maintenance of an effective attachment, connection, or seal between the endograft and the host aorta. Therefore dilatation of the aorta at the site or sites intended for primary endograft fixation may lead to treatment failure either with device migration or via the occurrence of a new endoleak with aneurysm expansion. The use of magnets as described in the present disclosure is intended to reduce the neck enlargement and remodeling since the magnet will distribute the stress more uniformly unlike the stent that pose stress concentration which induce vascular remodeling.

Endoleak is defined by the persistence of blood flow outside the lumen of the endoluminal graft but within the aneurysm sac, as determined by an imaging study. An endoleak is evidence of incomplete exclusion of the aneurysm from the circulation and may be the result of an incomplete seal between the endograft and the blood vessel wall, an inadequate connection between components of a modular prosthesis, fabric defects or porosity, or retrograde blood flow from patent aortic side branches. Hence, an adhesive force at the neck of the stent may minimize or prevent endoleak (type I).

Endoleaks, including their detection, potential clinical significance, and treatment remain an active area of investigation. However, although it is now evident that an endoleak may resolve spontaneously, a proportion of those that do persist have been associated with late aneurysm rupture. Endoleaks classification include:

1. Type I:
   a) Inadequate seal at the proximal end of endograft
   b) Inadequate seal at the distal end of endograft
   c) Inadequate seal at the iliac occluder plug
2. Type II: Flow from visceral vessels (lumbar, IMA, accessory renal, Hypogastric) without attachment site connection.
3. Type III:
   a) Flow from module disconnection
   b) Flow from fabric disruption (Minor<2 mm, Major>2 mm)
4. Type IV: Flow from porous fabric (<30 days after graft placement)

There are also endoleaks of undefined origins where flow is visualized but the source is unidentified.

Endotension. It is now appreciated as AAA may continue to enlarge after endovascular repair, even in the absence of detectable endoleak, and that this enlargement may lead to aneurysm rupture. Explanation for persistence or recurrent pressurization of an aneurysm sac includes blood flow that is below the sensitivity limits for detection with current imaging technology, or pressure transmission through thrombus, or endograft fabric. On physical examination, the aneurysm may be pulsatile and intrasac measurements may reveal pressure that approach or equal to systemic values. A magnetic device according to the present disclosure that provides sufficient "seal" at the two necks of the aneurysm and along the body of the aneurysm would eliminate endoleaks type I and II.

Migration. Migration is defined by clinical and radiographic parameters, as a caudal movement of the proximal attachment site or cranial movement of a distal attachment site. A device is considered to have migrated if at least 10 mm of movement was noted relative to anatomic landmarks, a patient experiences a symptom from migration, irrespective of distance, or a secondary intervention was undertaken to remedy migration-related problems, irrespective of distance. An adhesive force with sufficient shear component would also eliminate migration. Hence, one of the advantages of the present disclosure is the development of a magnet-based anchoring device at the two ends of the graft that overcomes endoleak and migration.

In biomedical engineering, the electromagnetic effect on biological cells has diverse applications such as MRI, bypass surgery, and MEMS-related devices. Static and time-dependent fields are used in the diagnosis and treatment of human disease. MRI involves using a large magnetic field to image structure. The therapeutic benefits of low frequency magnetic fields have been shown to induce gene expression and upregulate the heat shock protein. Recently, magnets are advocated for use in vascular coupling for distal anastomosis in bypass surgery, which has lead to a multi-center clinical trial. To date, most of the magneto-static research on biological cells is investigated by using analytic or numerical finite difference methods.

The fundamental equations governing the interaction between current and magnetic-flux density can be found in any classic textbook. In general, those equations are complex due to the fact that matter possesses a great variety of properties. For example, if the body of interest is elastic, then a change of shape, volume and temperature can appear. Also, if the sum of all forces acting on the body is not zero, translational or rotational acceleration may occur. Therefore, it is important to calculate the Magnetostatic forces and couple the Magnetostatic forces with other physical effects in order to determine the deformation, rotation, displacement and so on in the matter. In the present application, the force balance including the Maxwell's force is analyzed and simulated based on the distribution of the magnetic-flux density. The coupled formulation of the magnetic field and the surface stress balance for treatment of aortic aneurysm is demonstrated.

In general, the magnetic field intensity is not curl-free and, therefore, we cannot describe magnetic field intensity in terms of a scalar function. However, there are a number of important applications in magnetics in which a magnetic field exists, but there are no current densities involved. The most obvious are those involving permanent magnets. Here we consider a concentric annulus of the stent graft internal to the vessel lumen and the permanent magnetic ring external to the vessel wall as shown in FIG. 1. Since the magnetic ring does not cover the entire circumference of the vessel (covers 0 to 270°), the solution must be numerical. To design the geometry and magnetic properties of the two poles of the magnet (stent and magnetic ring) to produce the necessary Maxwell force acting on the aortic tissue that prevents migration, and endoleak.

A three-dimensional Laplace's equation describes the solution for the potential field in cylindrical coordinates ($\rho$, $\Phi$, z)

$$\frac{\partial^2 \Phi}{\partial \rho^2} + \frac{1}{\rho}\frac{\partial \Phi}{\partial \rho} + \frac{1}{\rho^2}\frac{\partial^2 \Phi}{\partial \phi^2} + \frac{\partial^2 \Phi}{\partial z^2} = 0 \tag{1}$$

The separation of variables is accomplished by the substitution:

$$\Phi(\rho,\phi,z)=R(\rho)Q(\phi)Z(z) \tag{2}$$

This leads to three ordinary differential equations:

$$\frac{d^2 Z}{dz^2} - k^2 Z = 0 \tag{3a}$$

$$\frac{d^2 Q}{d\phi^2} + v^2 Q = 0 \tag{3b}$$

$$\frac{d^2 R}{d\rho^2} + \frac{1}{\rho}\frac{dR}{d\rho} + \left(k^2 - \frac{v^2}{\rho^2}\right)R = 0 \tag{3c}$$

The solutions of the first two equations are elementary:

$$Z(z)=e^{\pm kz} \tag{4a}$$

$$Q(\phi)=e^{\pm v\phi} \tag{4b}$$

The radial equation can be put in a standard form by the change of variable x=k$\rho$. Then it becomes $$\frac{d^2 R}{dx^2} + \frac{1}{x}\frac{dR}{dx} + \left(1 - \frac{v^2}{x^2}\right)R = 0 \tag{5}$$

This is Bessel's equation, and the solutions are called Bessel functions of order v. When u=m is an integer and k is a constant to be determined. The radial factor is $$R(\rho)=CJ_m(k\rho)+DN_m(k\rho) \tag{6}$$

Finally, we get $$\Phi(\rho,\phi,z)=(Ae^{\pm kz})(Be^{\pm v\phi})[CJ_m(k\rho)+DN_m(k\rho)] \tag{7}$$

where A, B, and C are the unknown constant. If we combine equation (7) and boundary conditions, we can solve any type of magnetic field between the partial (0° to 270°) concentric annulus.

When the distribution of the magnetic field is known, the Maxwell's stress tensor can be calculated by the following formulation after the coordinate system transformation from the cylindrical coordinate to the rectangular coordinate.

$$T_{ij} = \frac{1}{\mu}\left[B_i B_j - \frac{1}{2}B^2 \delta_{ij}\right] \tag{8}$$

(Maxwell's Stress Tensor)
where $T_{ij}$: Maxwell's stress tensor [N/M$^2$, Newton/square meter); $\delta_{ij}$: Kronecker delta; $B_j$: magnetic-flux density T, Tesla or Wb/m$^2$, weber/meter$^2$]; $H_i$=$\mu B_i$; magnetic field intensity [N/(A·m), weber/(ampere·meter)]; $\delta_{ij}$=1 if i=j; $\delta_{ij}$=0 if i≠j.

In Matrix form, $$T_{ij} = \begin{bmatrix} \mu H_x^2 - \frac{1}{2}\mu|H|^2 & \mu H_x H_y & \mu H_x H_z \\ \mu H_x H_y & \mu H_y^2 - \frac{1}{2}\mu|H|^2 & \mu H_y H_z \\ \mu H_x H_z & \mu H_y H_z & \mu H_z^2 - \frac{1}{2}\mu|H|^2 \end{bmatrix} \tag{9}$$

(Maxwell's Stress Tensor)
Once the Maxwell's stress tensor is computed, the equilibrium force balance in the surface layer of the artery may be presented.

(Equilibrium equation for static case)

$$\sigma_{ji,j}+T_{ji,j}+f_i 0 \tag{10}$$

where $\sigma_{ji}$ is the stress tensor [N/M$^2$, Newton/square meter] and $f_i$ is the force [N/M$^3$, Newton/cubic meter].

Once the Maxwell stress is computed, we must calculate the Maxwell force. Elementary theory relates magnetostatic forces to changes in the total magnetic field energy when infinitesimal virtual displacements are made between magnetic elements.

$$F = \frac{\partial}{\partial R}\int \frac{B \cdot H}{2}dv \tag{11}$$

An alternative method using the Maxwell Stress Tensor allows magnetostatic forces to be calculated directly without approximating the limit of a virtual displacement. Instead, integration of the stress tensor $T_{ij}$ over any surface enclosing the object will give the net force acting on it directly if we assume that the permeability of the surrounding tissue (vessel wall and blood) is significantly different than that of the permanent magnets. If n is the outward normal to the surface, the Maxwell force may be computed as follows:

$$F = \int T_{ij} \cdot n ds \qquad (12)$$

Expanding the dot product $T_{ij} \cdot n$ allows the force integral equation (12) to be written explicitly as $$F = \frac{1}{\mu_0} \oint \left[ (B \cdot n)B - \frac{1}{2}B^2 n \right] ds = \mu_0 \oint \left[ (H \cdot n)H - \frac{1}{2}H^2 n \right] ds \qquad (13)$$

The stress vector $$P = \mu_0 \left[ (H \cdot n)H - \frac{1}{2}H^2 n \right] \qquad (14)$$

does not generally point along H. However for the two extreme cases of the H field either normal or parallel to the surface, the forces are either attractive or repulsive across the surface. But when the field crosses the surface at any other angle than 0° or 90°, there will be a shear component to the force which acts in the plane of the surface. When 3-D axis migration occurs, the magnetic fields H will change so that the axis force will be created in order to prevent the migration. This requires numerical method such as the FEM simulation.

An exemplary embodiment of the present disclosure as used in graft assembly 100 is shown in FIG. 1. Assembly 100 includes magnetic bodies 110 and magnetic polymer graft 111. In this embodiment, the magnetic bodies 110 may be situated at the proximal and distal ends of magnetic polymer graft 111 which may be positioned distal to the renal arteries 123 and proximal to the common iliac arteries 122 as shown in FIG. 1. The magnetic bodies 110 may cover part or the entire circumference of the abdominal aorta 120. The magnetic bodies 110 are shown to be ring-shaped in FIG. 1, but they can be any other shape (e.g., staple-shaped, etc.) as long as they are able to provide a sufficient magnetic attractive force on the magnetic polymer graft 111 to stabilize the magnetic polymer graft 111 on the inner surface of the aorta 120.

The magnetic polymer graft 111 may be situated inside the abdominal aorta 120 or the aneurysmic sac 121 and the magnetic bodies 110 may be situated external to the wall of the abdominal aorta 120 or the aneurysmic sac 121 as shown in FIG. 1. The magnetic bodies 110 may be composed of a material such that they produce a high magnetic field with a low mass and should be stable against demagnetization. When a ferromagnetic material is magnetized in one direction, it will not relax back to zero magnetization when the imposed magnetizing field is removed. The amount of magnetization it retains at zero driving field is defined as remanence. The amount of reverse driving field required to demagnetize it is called coercivity. Some compositions of ferromagnetic material will retain an imposed magnetization indefinitely and are useful as permanent magnets. NdFeB (Neodymium Iron Boron) is an example of a permanent magnet used in biological applications including sutureless vascular anastomosis with magnets.

The magnetic bodies 110 may stabilize the magnetic polymer graft 111 at the proximal and distal ends of the magnetic polymer graft 111 thereby preventing movement of the magnetic polymer graft 111 or endoleak or endotension. The magnetic polymer graft 111 may be uniformly composed of a metallic material commonly used in the medical arts such that the magnetic bodies 110 may exert an attractive force on the metallic material such that the magnetic polymer graft 111 is held in position by the magnetic bodies 110 on the proximal and distal ends of the magnetic polymer graft 1I as illustrated in FIG. 1. Alternatively, the magnetic polymer graft 111 may be composed of metallic material only at its proximal and distal ends such that the magnetic bodies 110 may be properly positioned to exert an attractive force on these proximal and distal ends of magnetic polymer graft 111. In this variation, the body of the magnetic polymer graft 111 may be mesh-like and may be composed of any material commonly used in the medical stenting arts (e.g., polytetrafluoroethylene—PTFE) such that it can house the metallic material at its proximal and distal ends. The magnetic polymer graft 111 may act as a stent by providing a structural passageway for blood to flow down the abdominal aorta 120 while avoiding contact with the aneurysmic sac 121.

A number of different delivery methods may be used to introduce the magnetic bodies 110 in place. Such methods are also applicable to the other exemplary embodiments presented below. Various delivery methods include, but are not limited to: (a) an abdominal laparoscopic procedure (AAA) or thoracoscopic procedure (TAA); (b) a minimal surgical procedure; or (c) an open surgical procedure. Other methods and procedures are apparent to one having ordinary skill in the art after consideration of the present exemplary embodiments and are, thus, within the scope of the present disclosure.

Another exemplary embodiment of the present disclosure is presented as assembly 200 and is shown in FIG. 1 Assembly 200 depicts a magnetic polymer graft 211 which includes a magnet cover 212, bonded magnet powder 213, and a graft lumen 214. The bonded magnet powder 213 of the magnetic polymer graft 211 may be composed of any material commonly used in the medical magnetic arts. The graft lumen 214 may be formed using materials commonly used in the medical stent arts (e.g., polytetrafluoroethylene—PTFE). The graft lumen 214 may allow blood to pass through its material and thereby prevent contact with the aneurysm (not shown) and it may be of such a diameter as to achieve the optimal or desired volume of blood flow through the aneurysm.

The magnetic polymer graft 211 may interact with magnetic bodies (not shown) situated on the external wall of the abdominal aorta or aortic aneurysm (not shown). In this way, the magnetic polymer graft 213 can be held in place by the attractive force being exerted on it by the magnetic bodies (not shown). Thus, the bonded magnet powder 213 can be situated inside a magnet cover 212 which may be the external layer of the magnetic polymer graft 211. The magnet cover 212 may act to protect and confine the magnet powder 213 and further serve to make contact with the inside of the abdominal aorta or aortic aneurysm. This configuration would provide the bonded magnetic powder 213 maximum communication with the magnetic bodies (not shown) situated on the external wall of the abdominal aorta or aortic aneurysm. The magnetic polymer graft 211 may be inserted through endovascular procedure into the patient thereby avoiding the complications associated with other invasive techniques.

Figure 3A:
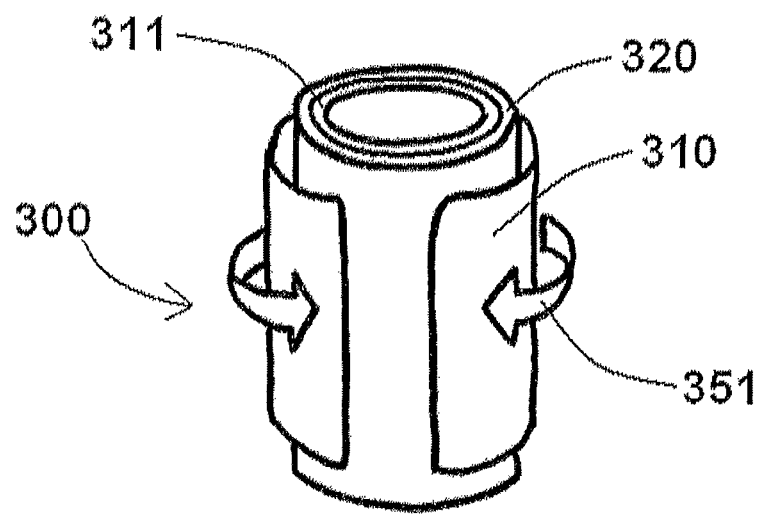
FIG. 3A shows a front view of a luminal stent graft embedded with magnetic beads or particles surrounded by a stabilizing magnetic body to prevent distension of the aneurysmic region according to an exemplary embodiment of the present disclosure.

Yet another exemplary embodiment of the present disclosure as shown in graft assembly 300 is presented in FIG. 3A. Assembly 300 includes magnetic body 310 and magnetic polymer graft 311. The magnetic body 310 is depicted as being ring-shaped in FIG. 3A but it may be any other shape as described above. The magnetic body 310 may cover part or the entire circumferential surface of the abdominal aorta 320. In the latter case, the magnetic body 310 may partially ensheathe the abdominal aorta 320 such that the magnetic body 310 is provided with enough surface area to interact with the magnetic polymer graft 311 on the inside of the abdominal aorta 320 thereby allowing a sufficient magnetic force to be applied to the magnetic polymer graft 311. The directional arrows 351 illustrate the manner in which the magnetic body 310 may ensheathe the abdominal aorta 320 (e.g., circumferentially) to allow for optimal interaction between the magnetic body 310 and the magnetic polymer graft 311.

Figure 3B:
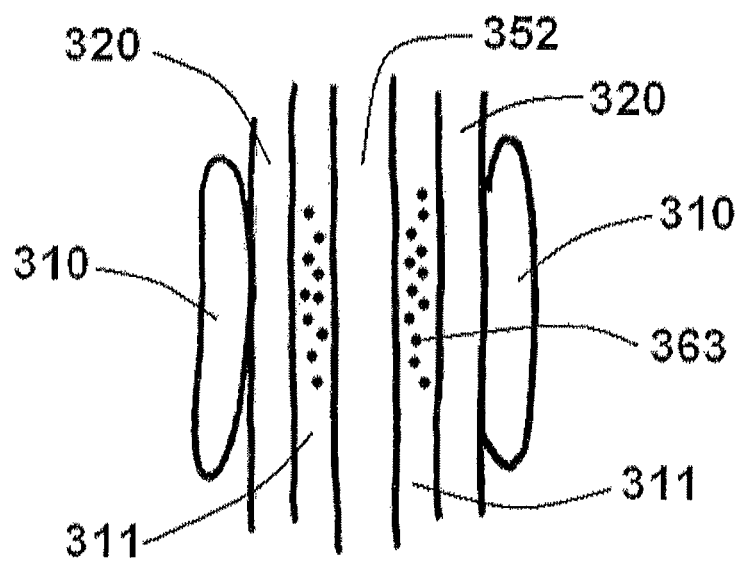
FIG. 3B shows a cross-section of FIG. 3A to emphasize axial support of the diseased region.

FIG. 3B shows a cross-section of assembly 300. The lumen 352 of the graft 311 may provide a conduit for the blood to flow through the aneurysmic sac (not shown) such that the blood flow does not contact the aneurysmic sac (not shown). The outer surface of the abdominal aorta 320 may be in physical contact with the magnetic body 310 as illustrated in FIG. 3B. The magnetic polymer graft 311 may make physical contact with the inner surface of the abdominal aorta 320 such that the magnetic polymer graft 311 is fitted tightly enough against the inner surface of the abdominal aorta 320 in order to prevent blood leakage out of the graft 311 and into the aneurysmic sac (not shown) via space between the proximal portion of the graft 311 and the inner surface of the abdominal aorta 320. This particular embodiment may also prevent endoleak type II and may further incorporate magnetic beads or particles 363 along the body of graft composite as shown in FIG. 3B. Application of magnetic body 310 external to the abdominal aorta 320 in the form of gel or glue on the adventitial surface may also provide a restrictive force which will prevent expansion of aorta against endoleak type II or endotension.

In this embodiment, we may consider the magnetic flux density B, which plays the significant role in the computation of attraction forces. The magnetic polymer graft 311 may include, for examples polymer-bonded Nd—Fe—B magnets (BNP-8) by compression moulding (polymer-bonding: magnet powders are mixed with a polymer carrier matrix, such as epoxy). The magnetic bodies 310 are formed in a certain shape, when the carrier is solidified, which has residual induction Br (0.6-0.65 Teslas or 6000-6500 Gauss); the ring consists of, for example, Heusler alloy ($Fe_{80} B_{20}$), which has the saturation magnetic flux density of 0.1257 Teslas (=1257 Gauss); or consists of carbon-coated metal particles, which has saturation magnetization exceeding about 120 emu/g (saturation magnetic flux density equal to or approximately 0.15 Teslas). The properties provide sufficient force to support the abdominal aorta 320.

Figure 4:
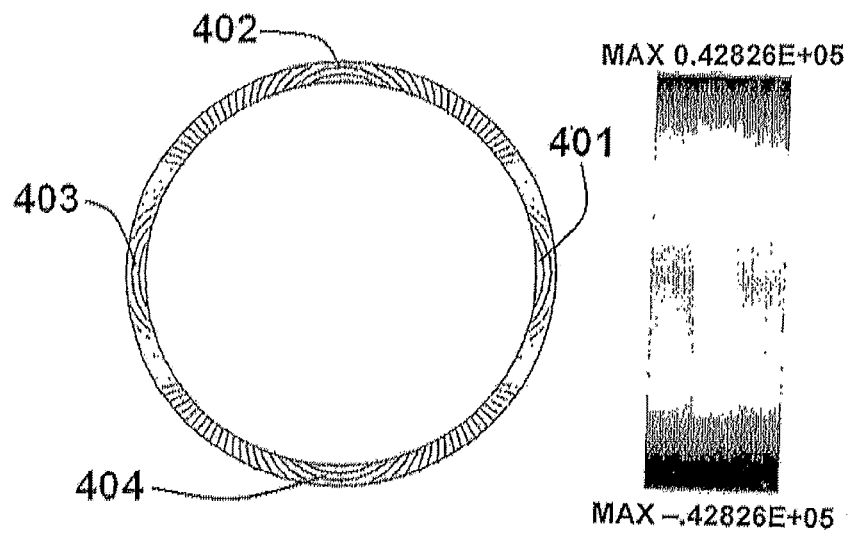
FIG. 4 shows $T_{11}$ changes with a maximum of $T_{11}$=42,826 KPa $\theta$=0° and 180° in the inner circular) and minimum of $T_{11}$=−42.826 KPa ($\theta$=90° and 270° in the inner circular) according to an exemplary embodiment of the present disclosure.

An exemplary measurement of the stress tension exerted on the blood vessel and the changes in $T_{11}$ (Maxwell's stress tensor wherein i=1 and j=1) are shown in FIG. 4 according to an exemplary embodiment of the present disclosure. The maximum stress tension is exerted on the vessel at 401 and 403 while the minimum stress tension is exerted on the vessel at 402 and 404 when an exemplary embodiment of the present disclosure is used to stabilize the graft to the inside wall of the vessel by placing magnetic bodies on the external surface of the vessel. This calculation demonstrates that the stress levels are within biologically acceptable ranges. In other words, the stress distribution demonstrates that the computed Maxwell stresses are well within the physiological range of tissue stress and should not harm the tissue. Hence, the present disclosure does not overly perturb the vessel wall and should not induce an injury response or remodeling.

Figure 5:
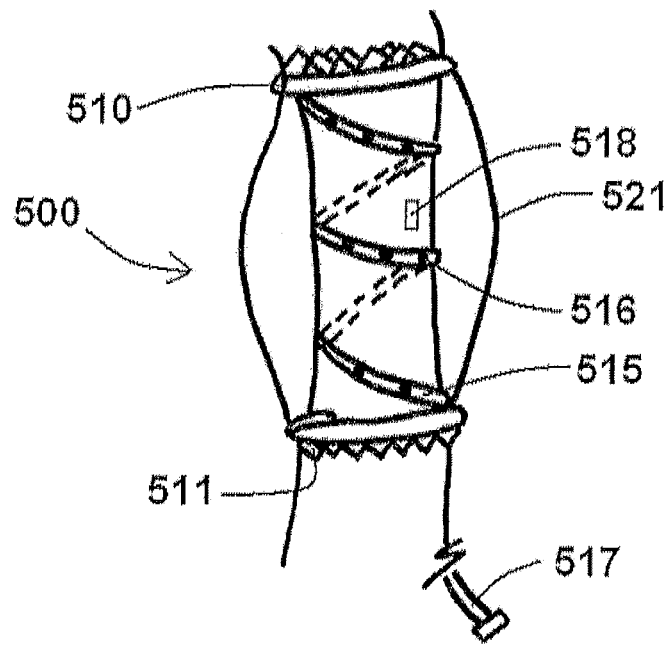
FIG. 5 shows a front view of a luminal stent graft within an aneurysm incorporating a perforated tube for controlling the fluid environment within the aneurysm and an optional pressure sensor as part of a telemetry system according to an exemplary embodiment of the present disclosure.

Another embodiment of the present disclosure comprises a graft assembly 500 as shown in FIG. 5. An exemplary assembly 500, as shown in FIG. 5, includes magnetic bodies 510, magnetic polymer graft 511, tube 515 with tube openings 516, a catheter 517, and an optional pressure sensor 518. Tube 515 with tube openings 516 may function to suck or siphon out accumulated blood and/or other tissue or matter and to collapse the wall of aneurysmic sac 521 to decrease bloodclot volume, which may reduce the stress in aneurysmic sac 521 after deployment of magnetic bodies 510 and decrease the risk of aneurysmic rupture.

Catheter 517 may be connected to tube 515 from the femoral artery such that a user is able to suction out accumulated blood and/or other matter. Alternatively, tube 515 and tube openings 516 may function as an embolization device such that a biocompatible liquid polymer (e.g., ethylene vinyl alcohol copolymer, cellulose, acetate polymer, cyanoacrylates or glue gel magnetic powder, or the like) may be introduced into aneurysmic sac 521 via catheter 517 and through tube openings 516 in order to pack aneurysmic sac 521 and thereby reduce the possibility of endoleak or endotension.

Tube 515 may be situated as shown in FIG. 5 on the outer surface of magnetic polymer graft 511 in a coiled configuration. Tube 515 may have tube openings 516 situated on the length of tube 515, and may be spaced apart and of such a diameter so that tube openings 516 may optimally function as described above. Additionally, tube openings 516 may be a slit or any other geometric shape including, but not limited to, a pyramid, in order to maximize the functioning of tube openings 516 as previously described.

In order to ensure efficient deployment of magnetic polymer graft 511 and magnetic bodies 510 (e.g., tight seal at the distal and proximal ends), it would be desirable to measure pressure in aneurysmic sac 521. An optional pressure sensor 518 may be situated on the outer surface of magnetic polymer graft 511 via mounting or gluing. Optional pressure sensor 518 may be in communication with an external telemetry monitoring system (not shown) via a wireless communication system (not shown). Optional pressure sensor 518 may be used to indicate whether or not a successful deployment of magnetic polymer graft 511 has been achieved. In this case, the measured pressure will yield a pulsatile tracing initially before deployment of magnetic bodies 510 and magnetic polymer graft 511. Once magnetic bodies 511 secure the proximal and distal ends of aneurysmic sac 521, a tight seal between magnetic bodies 510 and the surface of aneurysmic sac 521 would eliminate the pulsatile tracing. This would provide indication of successful deployment. This can equally apply to the current art of stent grafts without magnets.

Optional pressure sensor 518 may also be used to monitor the patient's aneurysm by measuring the pressure within aneurysmic sac 521. It may monitor the interior pressure of aneurysmic sac 521 by measuring the local pressure outside of the wall of magnetic polymer graft 511 and inside the outstretched wall of aneurysmic sac 521. This would be of tremendous clinical value as the physician can monitor the status of aneurysmic sac 521 and adapt treatment according to aneurysmic behavior. Currently, expensive and complicated imaging methods (such as MRI and CT) are used to monitor the dimension of the aneurysm longitudinally at discreet times (annually, etc.). Pressure is more relevant mechanically as a predictor of rupture and with telemetry it can be monitored continuously.

Figure 6A:
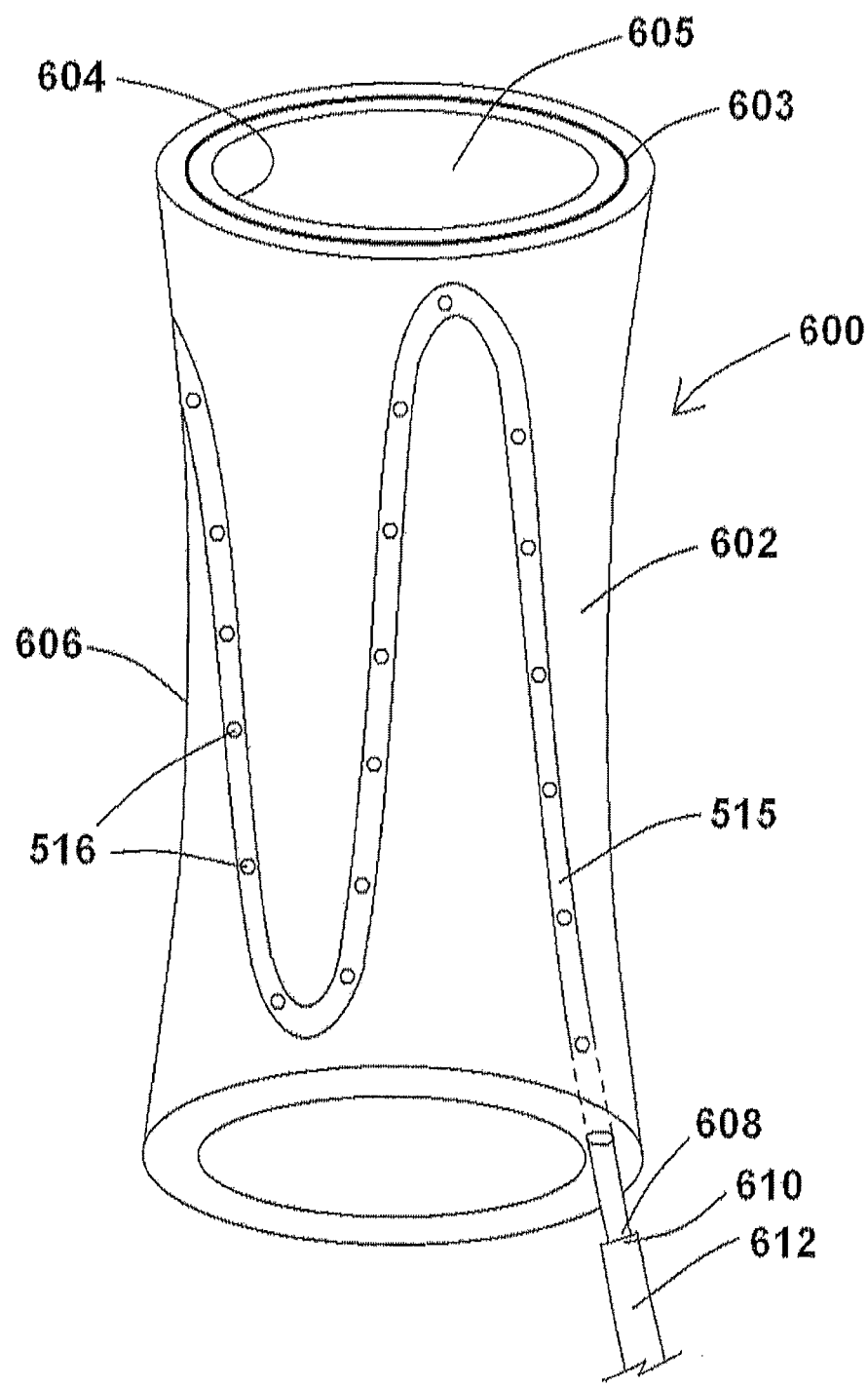
FIGS. 6A-6D show endograft assemblies according to exemplary embodiments of the present disclosure.

An additional embodiment of an endograft assembly of the present disclosure is shown in FIG. 6A. As shown in FIG. 6A, endograft assembly 600 comprises an endograft 602 having an inner wall 604, an outer wall 606, and a graft structure 603 positioned therebetween. Graft structure 603, in at least one embodiment, may be mesh-like and may be composed of any material commonly used in the medical stenting arts (e.g., various polymers and metals, including but not limited to PTFE). Graft structure 603, in various embodiments, may comprise a traditional stent, a balloon-expandable device, or an autoexpandable device. Inner wall 604 and outer wall 606 may comprise a fabric as described herein, or may comprise one or more other materials capable of permitting or prohibiting fluid flow therethrough as referenced herein. Inner wall 604 and outer wall 606 may be positioned a distance from one another, to permit graft structure 603 to be positioned therebetween, and further to permit a tube 515 having tube openings 516 to be positioned therebetween.

Inner wall 604 also defines an endograft lumen 605, as shown in FIG. 6A, permitting blood flow through a vessel when endograft assembly 600 is positioned therein. Tube openings 516 within tube 515 are effectively exposed along the outer wall 606 of endograft 602, whereby, for example, tube 515 has a sealed portion for passing from the walls of endograft 602 into a space outside of endograft 602. In another exemplary embodiment, tube 515 is incorporated into outer wall 606 so that tube openings 516 of tube 515 are exposed along the outer wall 606. In at least one embodiment, inner wall 604 is impermeable to fluids (i.e., blood), and outer wall 606 is permeable to fluids, including blood. Endograft 602 may comprise any number of additional features that typically or occasionally accompany endografts.

As shown in FIG. 6A, the proximal end 608 of tube 515 may be removably coupled to a distal end 610 of removable catheter 612. A suction/infusion source (not shown) may be coupled to the removable catheter 612 at or near the distal end 610 of removable catheter 612, so that fluid present in, for example, an aneurysm sac, may be removed by applying suction to or within removable catheter 612 so that the fluid may enter tube openings 516 of tube 515 as described herein.

Figures 6B, 6C:
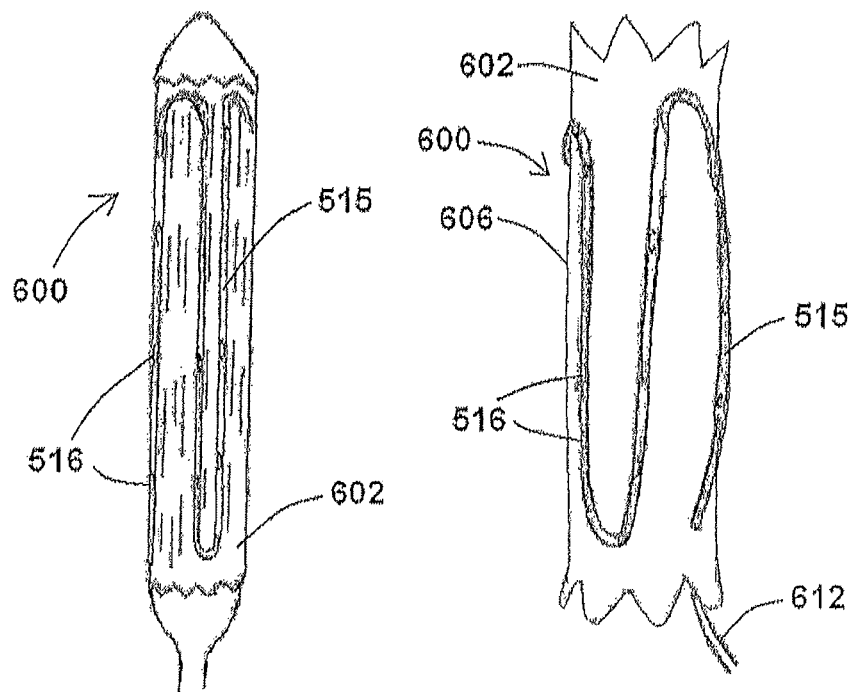
Figure 6D:
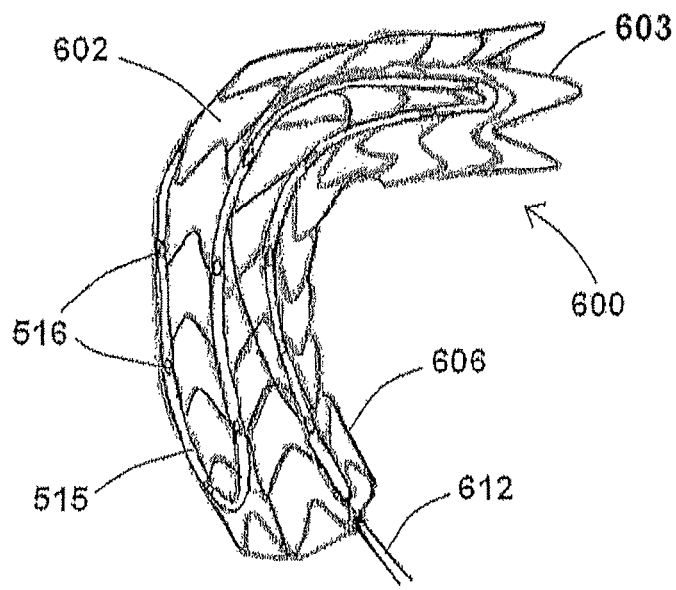

Additional embodiments of endograft assemblies 600 of the present disclosure are shown in FIGS. 6B-6D. In FIG. 6B, an exemplary endograft assembly 600 is shown in a collapsed configuration to permit, for example, insertion of endograft assembly 600 into a vessel. FIG. 6C shows an exemplary embodiment of an endograft assembly 600 of the present disclosure in an open or deployed configuration so that endograft assembly 600 may be used within the body as referenced herein. In at least one embodiment, endograft assembly 600 may be opened or deployed by way of moving/pulling a portion of endograft assembly 600 relative to another portion, similar to the deployment of a stent, so that graft structure 603 of endograft 602 may expand from a collapsed configuration. In at least this example, tube 515 is incorporated into or positioned upon outer wall 606, so that tube openings 516 of tube 515 are exposed along the outer wall 606 of endograft 602. Such an exemplary endograft assembly 600 may be useful in connection with, for example, treating an abdominal aortic aneurysm. In addition, and as shown in FIG. 6C, removable catheter 612 is coupled to tube 515, with a sealed entrance of tube 515 through the outer wall 606 of endograft assembly 600.

Another exemplary embodiment of an endograft assembly 600 of the present disclosure is shown in FIG. 6D. As shown in FIG. 6D, the exemplary endograft assembly 600 comprises a curved configuration, which may be useful to treat, for example, a thoracic aortic aneurysm. An exemplary embodiment of an endograft assembly 600 of the present disclosure is shown in FIG. 6E as a block diagram with identified functional components, wherein said system comprises, for example, an endograft 602 comprising a graft structure 603, a tube 515, a removable catheter 612, and a suction/infusion source 614 (such as, for example, a syringe).

Figure 7:
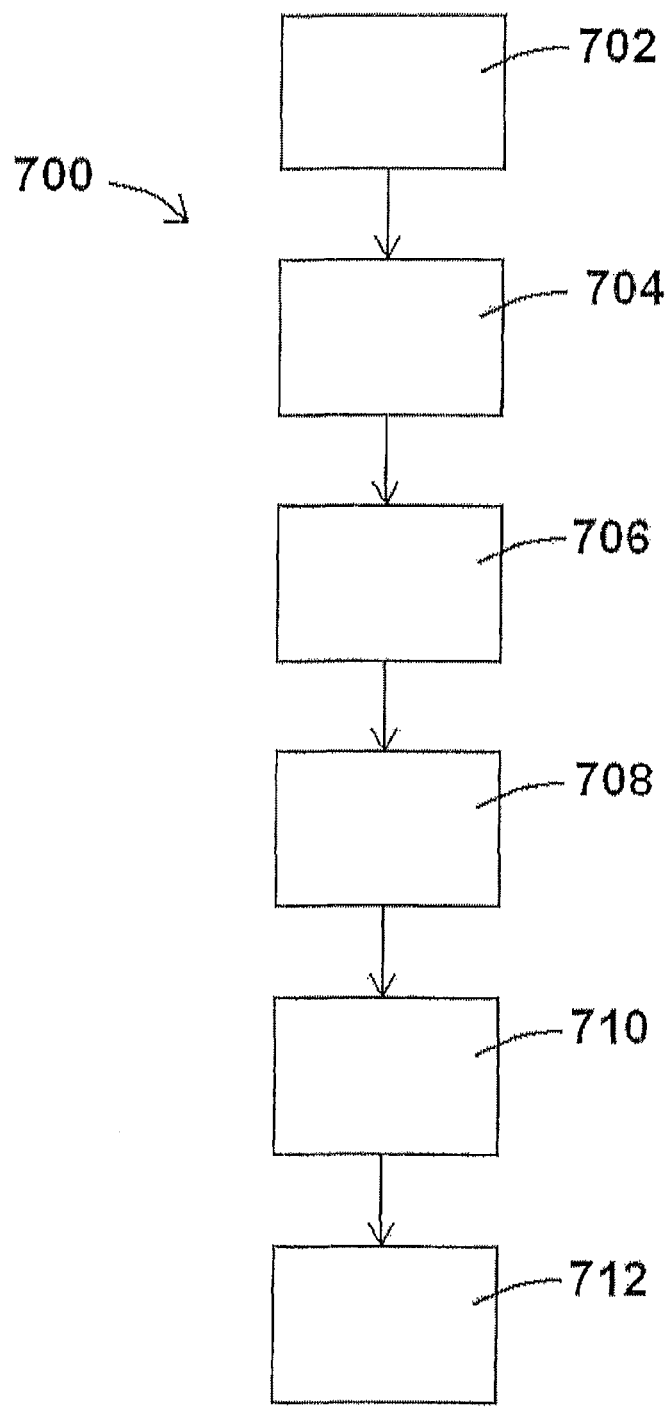
FIG. 7 shows a diagram of a method for using an endograft assembly according to an exemplary embodiment of the present disclosure.

An exemplary endograft assembly 600, including the endograft assembly 600 shown in FIG. 6A, may be used by performing the following method. Steps of an exemplary method 700 for deploying and using an endograft assembly 600 of the present disclosure are shown in FIG. 7. As shown in FIG. 7, method 700 may comprise the step of delivering an endograft assembly 600 to a desired site within a body, including, but not limited to, an aneurysm sac (an exemplary delivery step 702). This step may be performed using any number of methods for delivering endografts, stents, and/or other implantable devices within a human body, so long as removable catheter 612 either remains affixed to tube 515 or is ultimately connected to tube 515, so that a suction/infusion source 614 coupled to removable catheter 612 may be used as referenced herein. After endograft assembly 600 is positioned within a vessel, graft portion 603 of endograft assembly 600 may be opened/deployed from a closed/collapsed configuration (an exemplary deployment step 704) to secure endograft assembly 600 within said vessel.

After endograft assembly 600 is deployed within the vessel, suction from a suction/infusion source 614 may be used (an exemplary suction step 706) to withdraw, for example, blood, blood clots, and/or other particulates from an aneurysm sac, by way of blood and/or other materials entering tube openings 516 of tube 515 present within/about endograft assembly 600. Performance of suction step 706 may also cause the walls of aneurysm sac to collapse about endograft assembly 600. The degree to which said walls may collapse about endograft assembly 600 depends on the relative thickness of said sac/vessel walls.

After removal of fluid from the area of interest, suction/infusion source 614 may be used to inject a substance (an exemplary injection step 708) into, for example, the aneurysm sac. Such a substance may comprise any number of biocompatible liquids including, but not limited to, various polymers such as ethylene vinyl alcohol (EVOH) copolymer, acetate polymer, EVOH dissolved in dimethyl sulfoxide (DMSO), cellulose, various cyanoacrylates (such as 2-octyl cyanoacrylate, n-butyl cyanoacrylate, iso-butyl-cyanoacrylate, and/or methyl-2- or ethyl-2-cyanoacrylate, for example), various glues/(such as fibrin glues, ultraviolet-light-curable glues, collagen-based glues, and/or resorcinol-formaldehyde glues, for example), various sealants (such as albumin based sealants and/or hydrogel sealants—eosin based primer having a copolymer of polyethylene glycol with acrylate end caps with a sealant of polyethylene glycol plus polylactic acid, for example), gel magnetic polymer, gelatin-resorcinol-formaldehyde, styrene-derivatized (styrenated) gelatin, poly (ethylene glycol) diacrylate (PEGDA), polylactic-co-glycolic acid) (PLGA), carboxylated camphorquinone in phosphate-buffered saline (PBS), polymethylmethacrylate, vascular endothelial growth factor, fibroblast growth factor, hepatocyte growth factor, connective tissue growth factor, placenta-derived growth factor, and/or angiopoietin-1 or granulocyte-macrophage colony-stimulating factor, for example.

Injection of such substances into the aneurysm sac would be performed to strengthen/reinforce the weakened aneurysm sac walls (forming a rigid or semi-flexible cast) to reduce the likelihood of or prevent aneurysm rupture, which can be fatal in many instances. Said substances may also prevent the migration of an endograft assembly 600 within the vessel by adhering to said assembly 600.

After all suction and injection steps have been performed, removable catheter 612 would be disconnected from tube 515 (an exemplary catheter disconnection step 710) so that the endograft assembly 600 would be separate from removable catheter 612. Removable catheter 612 may then be withdrawn from the patient's body (an exemplary catheter withdrawal step 712), allowing the endograft assembly 600, with substance 806 (as shown in FIG. 8C, for example) positioned external to assembly 600 to reinforce weakened aneurysm sac walls, to remain within the body.

An exemplary embodiment of an endograft assembly 600 of the present disclosure is shown in FIGS. 8A-8C. As shown in FIG. 8A, endograft assembly 600 has been inserted, positioned, and deployed within vessel 800 at a site of an aneurysm sac 802, which is presumably filled with blood, blood clots, and/or other particulates. The application of suction via removable catheter 612 by way of a suction/infusion source (not shown) operates to remove the blood, blood clots, and/or other particulates, allowing the distended vessel wall 804 to collapse or revert back to a relatively native configuration as shown in FIG. 8B. Reinforcement of the vessel wall 804 at the site of aneurysm may be performed by injection step 708 of the method described herein, whereby a substance 806 is injected using suction/infusion source through removable catheter 612, through tube 515, and out of tube openings 516 into the space surrounding endograft assembly 600 at the site of aneurysm. FIG. 8C depicts this procedure, with the black dots representing injected substance 806.

FIGS. 9A-9C show exemplary embodiments of a portion of an endograft assembly 600 and at least one embodiment of connecting and disconnecting a tube 515 of endograft assembly 600 to/from removable catheter 612 (also referred to as an intra-stent graft connection). As shown in FIG. 9A, an exemplary embodiment of a removable catheter 612 may comprise a catheter tip 900 configured to fit within the internal lumen 902 of tube 515. Removable catheter 612, in at least one embodiment, may comprise a first threaded portion 904 at or near the distal end 610 of removable catheter 612, said first threaded portion 904 corresponding to a second threaded portion 906 within tube 515 at or near the proximal end 608 of tube 515. Tube 515, in an exemplary embodiment, may comprise one or more unidirectional valves 908, said valves 908 permitting fluid to flow in and out of tube 515 while removable catheter 612 is coupled thereto (and when unidirectional valves 908 are in a first, open configuration), but preventing fluid from flowing out of tube 515 when removable catheter 612 is disconnected from tube 515 (and when unidirectional valves 908 are in a second, closed configuration) as shown in FIG. 9C. Furthermore, and when unidirectional valves 908 are closed, blood from the vessel to which endograft assembly 600 is positioned is prevented from exiting tube 515.

Removal of removable catheter 612 from tube 515 may be performed as shown in FIG. 9B. As shown in FIG. 9B, removable catheter 612 may be rotated in a direction indicated by the arrow shown in the figure (or rotated in an opposite direction depending on the configuration of the first threaded portion 904 and the second threaded portion 906), whereby said rotation would allow removable catheter 612 to detach from tube 515, in the direction of the arrow shown in FIG. 9C, permitting removal of removable catheter 612 from the body (at, for example, a patient's femoral artery). Rotation of removable catheter 612, as well as operation of suction/infusion source 614 as referenced herein, may be performed by a user external to a patient's body.

Additional embodiments of mechanisms for connecting and disconnecting tube 515 from removable catheter 612 are also contemplated by the present disclosure. Such mechanisms may include, but are not limited to, pulling removable catheter 612 with enough force to detach removable catheter 612 from tube 515, magnetic coupling of removable catheter 612 to tube 515, and other mechanisms known in the art for connecting and disconnecting two tubes.

Figure 10:
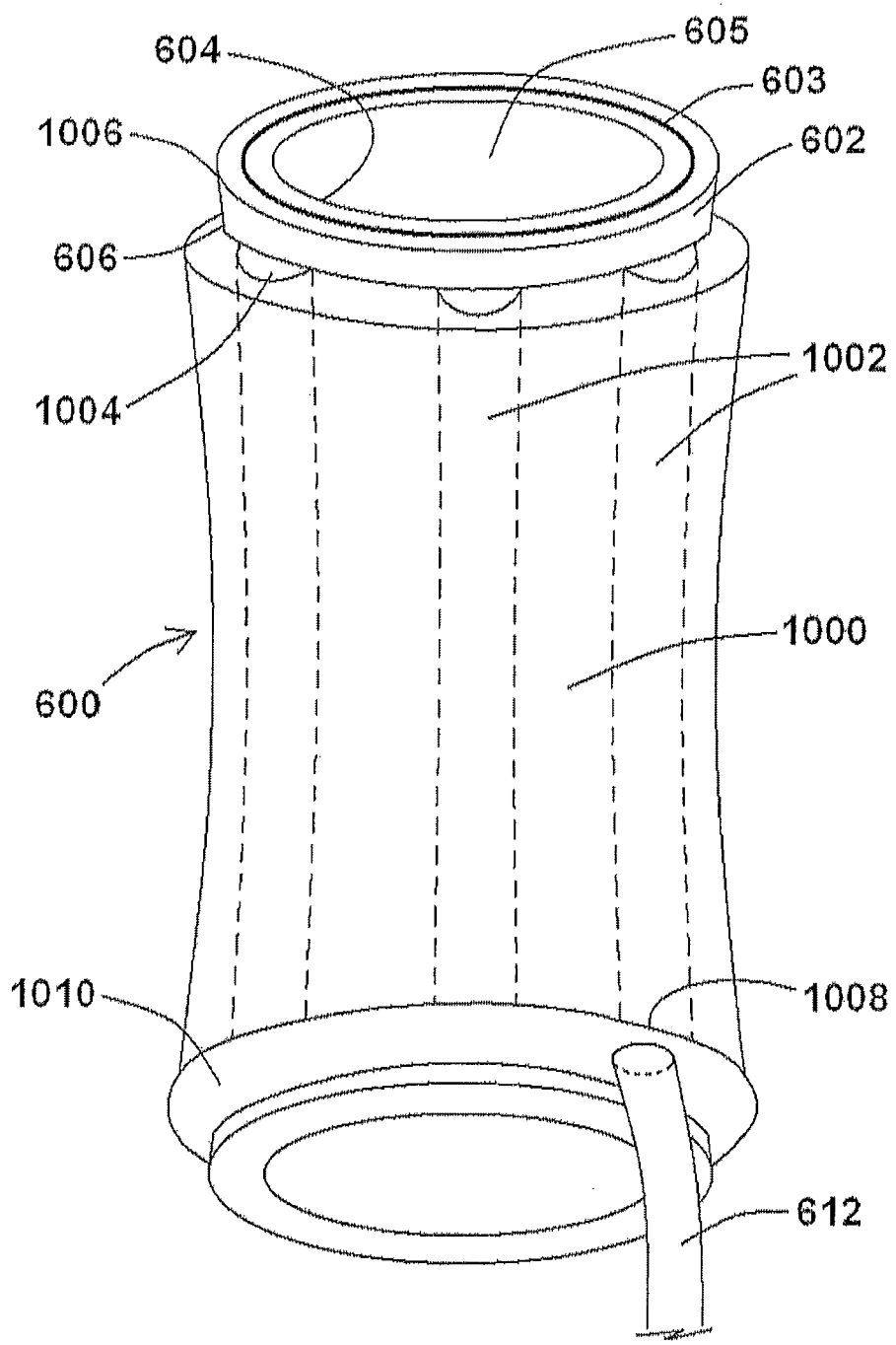
FIG. 10 shows an endograft assembly comprising a sponge sheath according to an exemplary embodiment of the present disclosure.

An additional embodiment of an endograft assembly 600 of the disclosure of the present application is shown in FIG. 10. As shown in FIG. 10, endograft assembly 600 comprises an endograft 602 having an inner wall 604, an outer wall 606, a graft structure 603 positioned therebetween, and further comprising a sponge sheath 1000 positioned around at least a portion of the outer wall 606 of endograft 602. Inner wall 604 defines an endograft lumen 605, as shown in FIG. 10, permitting blood flow through a vessel when endograft assembly 600 is positioned therein. In at least one embodiment, inner wall 604 is impermeable to fluids (i.e., blood), and outer wall 606 is permeable to fluids, including blood. Sponge sheath 1000 may comprise any number of biocompatible spongy (porous) materials including, but not limited to, cellulose/wood fibers, various foamed plastic polymers, polyurethane, silastic, rubber, PTFE, synthetic sponges, natural sponges, low-density polyether (also known as the rainbow packs of non-absorbent sponges), polyvinyl alcohol (PVA), and polyester. Sponge sheath 1000, in at least one embodiment, is positioned circumferentially around the outer wall 606 of endograft 602, but does not cover either end of said endograft 602.

In at least one embodiment, and as shown in the exemplary embodiment of the endograft assembly 600 shown in FIG. 10, one or more sponge channels 1002 are defined within sponge sheath 1000. Sponge channels 1002 may, as shown in the exemplary embodiment shown in FIG. 10, have open distal ends 1004 at or near the distal end 1006 of endograft 602, and the proximal ends 1008 of sponge channels 1002, at or near the proximal end of endograft 602, are in fluid communication with a reservoir bag 1010 coupled to sponge sheath 1000. Sponge channels 1002 may be parallel to one another (as shown in FIG. 10), or may comprise a perpendicular, radial, or net configuration. Reservoir bag 1010 may be collapsible, and may comprise any number of materials as referenced herein in connection with various endograft assemblies and/or components.

Additional embodiments of exemplary endograft assemblies 600 (and portions thereof) of the present disclosure are shown in FIGS. 11A-11C. As shown in FIG. 11A, an exemplary endograft assembly 600 comprises an endograft 602 comprising a graft structure 603, a sponge sheath 1000 (identified by the numerous ovals to visually depict the pores of a sponge), and a reservoir bag 1010 coupled thereto. The endograft assembly 600 shown in FIG. 11A is shown in a collapsed configuration to permit, for example, insertion of endograft assembly 600 into a vessel. FIG. 11B shows an exemplary embodiment of an endograft assembly 600 of the present disclosure in an open or deployed configuration so that endograft assembly 600 may be used within the body as referenced herein. The exemplary endograft assembly is also shown in FIG. 11B with a removable catheter 612 removably coupled to reservoir bag 1010, so that blood removed from the aneurysm cavity from sponge sheath 1000 that enters reservoir bag 1010 may be removed using removable catheter 612.

A portion of an exemplary endograft assembly 600 of the present disclosure is shown in FIG. 11C. As shown in the portion of endograft assembly 600 shown in FIG. 11C, endograft assembly 600 comprises an endograft 602 comprising a graft structure 603, a sponge sheath 1000, and sponge channels 1002 having distal ends 1004 at the distal end 1006 of endograft 602.

Figure 12B:
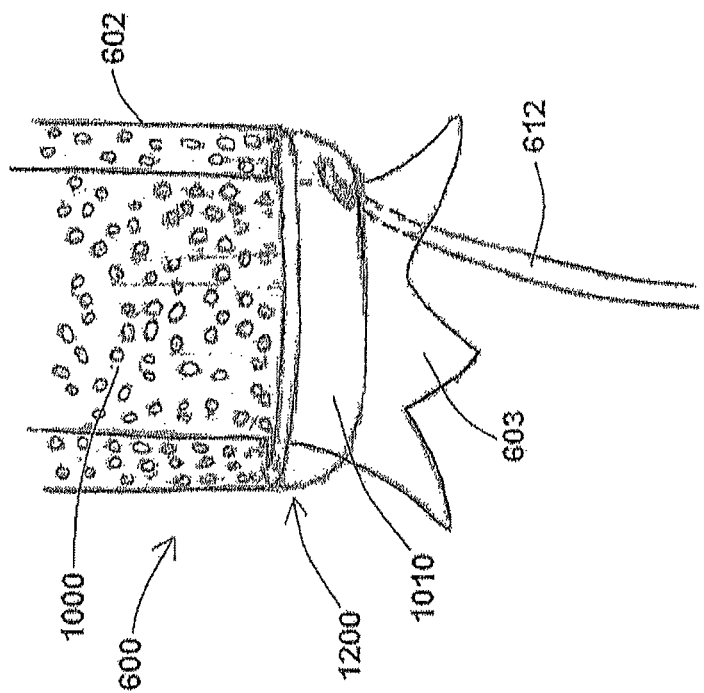
Figure 12A:
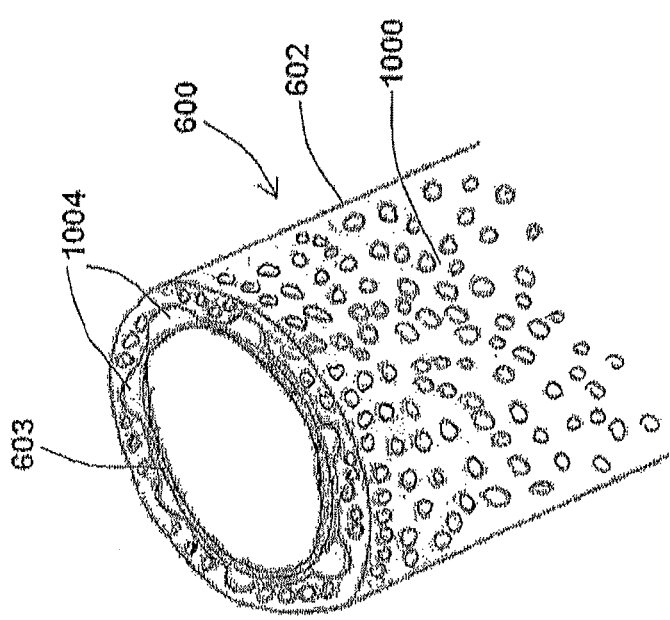

Additional embodiments of portions of exemplary endograft assemblies 600 of the present disclosure are shown in FIGS. 12A and 12B. As shown in FIG. 12A, endograft assembly 600 comprises an endograft 602 surrounded by a sponge sheath 1000. At the distal end of endograft 602, sponge channels 1004 are visible within sponge sheath 1000 as shown in FIG. 11C. FIG. 12B shows a portion of an exemplary endograft assembly 600, whereby a reservoir bag 1010 is coupled to a sponge sheath 1000 at or near the proximal end 1200 of endograft assembly 600. A removable catheter 612 is also shown in FIG. 12B coupled to reservoir bag 1010. Removable catheter 612 may be removably coupled to reservoir bag 1010 in the same or similar manner as removable catheter 612 is coupled to tube 515 as shown in FIGS. 9A-9C, or removable catheter 612 may be removably coupled to reservoir bag 1010 as referenced below.

FIGS. 13A-13C show exemplary embodiments of a portion of an endograft assembly 600 and at least one embodiment of connecting and disconnecting a reservoir bag 1010 of endograft assembly 600 to/from removable catheter 612. As shown in FIG. 13A, an exemplary embodiment of a removable catheter 612 comprises a catheter tip 900 configured to fit within the internal space 1300 of reservoir bag 1010. Removable catheter 612, in at least one embodiment, may comprise a first threaded portion 904 at or near the distal end 610 of removable catheter 612, said first threaded portion 904 corresponding to a second threaded portion 1302 within reservoir bag 1010. Reservoir bag 1010, in an exemplary embodiment, may comprise one or more unidirectional valves 1304, said valves 1304 permitting fluid to flow in and out of reservoir bag 1010 while removable catheter 612 is coupled thereto (and when unidirectional valves 1304 are in a first, open configuration), but preventing fluid from flowing out of reservoir bag 1010 when removable catheter 612 is disconnected from reservoir bag 1010 (and when unidirectional valves 1304 are in a second, closed configuration) as shown in FIG. 13C. Furthermore, and when unidirectional valves 1304 are closed, blood from the vessel to which endograft assembly 600 is positioned is prevented from exiting reservoir bag 1010. In addition, and as shown in FIGS. 13A-13C, a stent graft wall 1306 may be positioned at or near the portion of reservoir bag 1010 to receive removable catheter 612, whereby stent graft wall 1306 provides reinforcement so that reservoir bag 1010 does not collapse about removable catheter 612.

Removal of removable catheter 612 from reservoir bag 1010 may be performed as shown in FIG. 13B. As shown in FIG. 13B, removable catheter 612 may be rotated in a direction indicated by the arrow shown in the figure (or rotated in an opposite direction depending on the configuration of the first threaded portion 904 and the second threaded portion 1302), whereby said rotation would allow removable catheter 612 to detach from reservoir bag 1010, in the direction of the arrow shown in FIG. 13C, permitting removal of removable catheter 612 from the body (at, for example, a patient's femoral artery). Rotation of removable catheter 612, as well as operation of suction/infusion source 614 as referenced herein, may be performed by a user external to a patient's body.

Additional embodiments of mechanisms for connecting and disconnecting reservoir bag 1010 from removable catheter 612 are also contemplated by the present disclosure. Such mechanisms may include, but are not limited to, pulling removable catheter 612 with enough force to detach removable catheter 612 from reservoir bag 1010, magnetic coupling of removable catheter 612 to reservoir bag 1010, and other mechanisms known in the art for connecting and disconnecting a tube from a reservoir.

Figure 14:
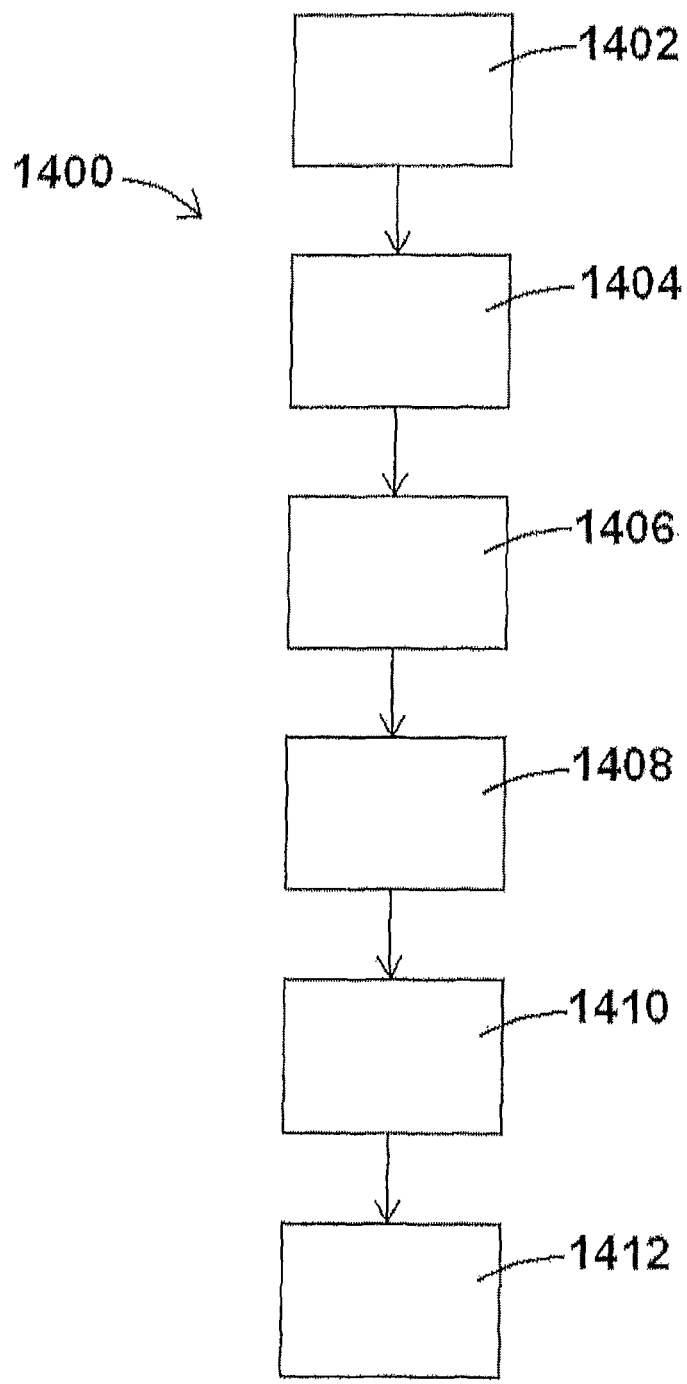
FIG. 14 shows a diagram of a method for using an endograft assembly according to an exemplary embodiment of the present disclosure.

An exemplary endograft assembly 600, including the endograft assemblies 600 shown in FIGS. 10-13C, may be used by performing the following exemplary method 1400 for deploying and using an endograft assembly 600 of the present disclosure shown in FIG. 14. As shown in FIG. 14, method 1400 may comprise the step of delivering endograft assembly 600 to a desired site within a body, including, but not limited, an aneurysm sac (an exemplary delivery step 1402). This step may be performed using any number of methods for delivering endografts, stents, and/or other implantable devices within a body known in the art, so long as removable catheter 612 remains affixed to reservoir bag 1010 or is ultimately connected to reservoir bag 1010, so that a suction/infusion source 614 coupled to removable catheter 612 may be used as referenced herein. After endograft assembly 600 is positioned within a vessel, graft portion 603 of endograft assembly 600 may be opened/deployed from a closed/collapsed configuration (an exemplary deployment step 1404) to secure endograft assembly 600 within said vessel.

After endograft assembly 600 is deployed within a vessel, suction from a suction/infusion source 614 may be used (an exemplary suction step 1406) to withdraw, for example, blood, blood clots, and/or other particulates from an aneurysm sac, by way of blood entering sponge channels 1002 of sponge sheath 1000 present around endograft assembly 600, entering reservoir bag 1010, and exiting out of removable catheter 612. Performance of suction step 1406 may also cause the walls of aneurysm sac to collapse about endograft assembly 600, which depends on the relative thickness of said sac/vessel walls.

After removal of fluid from the area of interest, suction/infusion source 614 may be used to inject a substance (an exemplary injection step 1408) into, for example, the aneurysm sac. Such a substance may comprise any number of biocompatible liquids including, but not limited to, various polymers such as ethylene vinyl alcohol (EVOH) copolymer, acetate polymer, EVOH dissolved in dimethyl sulfoxide (DMSO), cellulose, cyanoacrylates, various glues, and gel magnetic polymer. Injection of such substances from removable catheter 612, through sponge sheath 1000, and into the aneurysm sac would be performed to strengthen/reinforce the already weakened aneurysm sac walls (forming a cast) to reduce or prevent the likelihood of aneurysm rupture, which can be fatal in many instances. Said substances may also prevent the migration of an endograft assembly 600 within the vessel by adhering to said assembly 600.

After all suction and injection steps have been performed, removable catheter 612 would be disconnected from reservoir bag 1010 (an exemplary catheter disconnection step 1410) so that the endograft assembly 600 would be separate from removable catheter 612. Removable catheter 612 may then be withdrawn from the patient's body (an exemplary catheter withdrawal step 1412), allowing the endograft assembly 600, with a substance 806 positioned external to assembly 600 to reinforce weakened aneurysm sac walls, to remain within the body.

Use of an exemplary endograft assembly 600 consistent with method 1400 is shown in FIGS. 15A and 15B. As shown in FIG. 15A, endograft assembly 600 is positioned within a vessel 800 at the site of an aneurysm (identified by aneurysm sac 802 and distended vessel wall 804). Upon removal of blood from aneurysm sac 802 (via suction step 1406, for example) through sponge sheath 1000, into reservoir bag 1010, and out from removable catheter 612, one or more substances 806 may be injected into aneurysm sac 802 as shown in FIG. 15B (via injection step 1408, for example). The injected substance 806 (represented by the black dots in FIG. 15B) may form a cast as referenced herein, reinforcing the vessel walls 804 at the site of an aneurysm.

Figure 16:
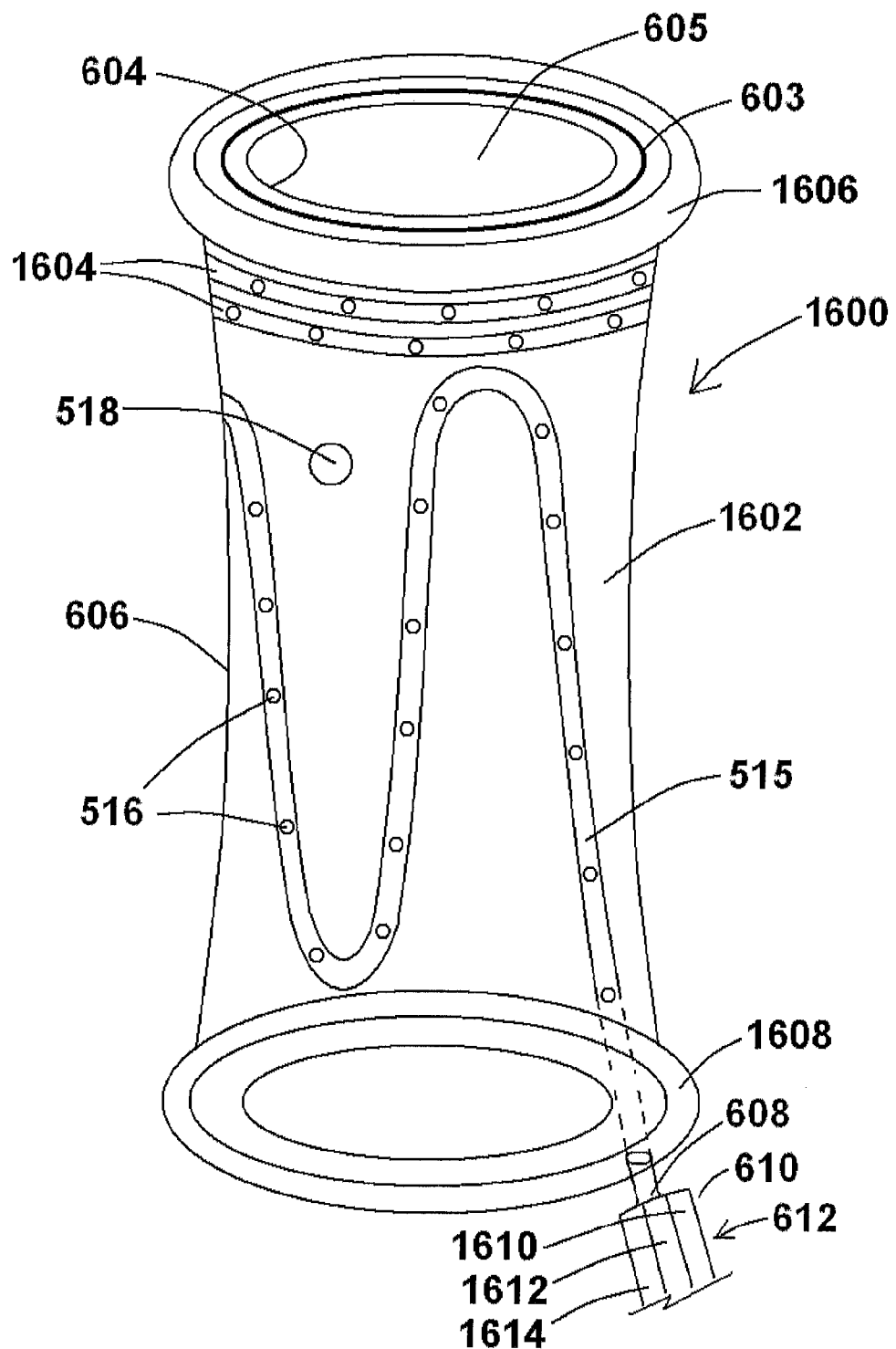
FIGS. 16 and 17 show perspective front views of endoprosthesis assemblies according to exemplary embodiments of the present disclosure.

An exemplary embodiment of an endoprosthesis assembly 1600 of the present disclosure is shown in FIG. 16. As shown in FIG. 16, endoprosthesis assembly 1600 comprises an endoprosthesis 1602 comprising an inner wall 604, an outer wall 606, and optionally an additional structure 603 positioned between inner wall 604 and outer wall 606. Endoprosthesis assembly 1600, in such an embodiment, has an inner wall 604 that is impermeable to fluids (i.e., blood), and an outer wall 606 that is permeable to fluids, including blood, as described herein with respect to various endograft assembly 600 embodiments.

A tube 515 having tube openings 516, as shown in FIG. 16, may be positioned upon or within outer wall 606. In at least one exemplary embodiment, and as shown in FIG. 16, endoprosthesis assembly 1600 comprises a first tube 515 extending in various directions upon or within outer wall 606, such as in a back and forth "S" pattern as shown therein. Furthermore, and as shown in FIG. 16, endoprosthesis assembly 1600 may comprise one or more second tubes 1604 having tube openings 516 defined therein, wherein second tube 1604 extends circumferentially around or within outer wall 606. In at least one embodiment, a single tube 515 or 1604 may be used in a back and forth "S" pattern and in a complete or partial circumferential pattern. In various other embodiments, tubes 515 and/or 1604 may have any number of other configurations about endoprosthesis 1602. As shown in FIG. 16, for example, the circumferential arrangement of tube(s) 1604 (noting that more than one tube 1604 may be present) allows for a more concentrated and/or higher quantity/volume of a casting material to be delivered locally to such an arrangement as described in further detail herein.

Inner wall 604 also defines a lumen 605, as shown in FIG. 16, permitting blood flow through a bodily vessel when endoprosthesis assembly 1600 is positioned therein. Tube openings 516 within tube(s) 515, 1604, in various embodiments, are effectively exposed along and/or within the outer wall 606 of endoprosthesis 1602, whereby, for example, tube(s) 515, 1604 have a sealed portion for passing from the walls of endoprosthesis 1602 into a space outside of endoprosthesis 1602. In another exemplary embodiment, tube(s) 515, 1604 are incorporated into outer wall 606 so that tube openings 516 of tube(s) 515, 1604 are exposed along the outer wall 606. An exemplary endoprosthesis 1602 of the present disclosure may comprise any number of additional features that typically or occasionally accompany endografts or endoprostheses.

As shown in FIG. 16, the proximal end 608 of tube 515 may be removably coupled to a distal end 610 of removable catheter 612. In various other embodiments, removable catheter 612 may couple to other components of endoprosthesis assembly 1600, such as, for example, tube 1604, outer wall 606, and/or one or more connectors as described in further detail herein. A suction/infusion source (not shown) may be coupled to the removable catheter 612 at or near the distal end 610 of removable catheter 612, so that fluid present in, for example, an aneurysm sac, may be removed by applying suction to or within removable catheter 612 so that the fluid may enter tube openings 516 of tube(s) 515, 1604 as described herein.

In addition, and as shown in FIG. 16, various embodiments of endoprosthesis assemblies 1600 of the present disclosure comprise a distal balloon 1606 and a proximal balloon 1608, said balloons 1606, 1608 capable of inflation and deflation. Balloons 1606, 1608 would be either directly or indirectly coupled to catheter 612 so that an inflation/deflation source (not shown) may be coupled to catheter 612 to inflate and/or deflate balloons 1606, 1608. For example, inflation/deflation source could be a source of carbon dioxide, saline, saline mixed with a radiopaque contrast, radiopaque dye, or another gas and/or liquid, and injection of the same could be used to inflate and subsequently deflate balloons 1606, 1608. Use of such a substance that is radiopaque, for example, could allow balloons 1606, 1608 to be viewed using an angiogram, for example, so that a physician can locate the endoprosthesis assembly within the patient. As shown in FIG. 16, balloons 1606, 1608 are ring-shaped, so that when endoprosthesis assembly 1600 is positioned within a luminal organ, inflation of balloons 1606, 1608 can effectively secure assembly 1600 within the vessel and can also prevent endoleak and/or leakage of casting material past the boundaries of endoprosthesis assembly 1600.

As shown in FIG. 16, an embodiment of removable catheter 612 of the present disclosure would define multiple lumens. For example, removable catheter 612 may define a first lumen 1610 in communication with one or more of the first tube 515 and second tube 1604 so that a suction/infusion source coupled thereto could provide suction or inject a substance therethrough. Removable catheter 612 may further define a second lumen 1612 indirectly or directly in communication with one or more of balloons 1606, 1608 so that an inflation/deflation source coupled thereto could be used to inflate and/or deflate balloons 1606, 1608. In yet another embodiment, removable catheter 1604 may further define a third lumen 1614 to provide a casting material from a casting material source. In at least another embodiment, for example, first lumen 1610 is in communication with first tube 515, second lumen 1612 is in communication with one or more of balloons 1606, 1608, and third lumen is in communication with second tube 1604.

In addition to the foregoing, an optional pressure sensor 518 may be situated on the outer surface of endoprosthesis 1602 (as shown in FIG. 16, for example), or may be positioned in communication with one or more tubes/connectors of endoprosthesis assembly 1600 to facilitate pressure measurements in the vicinity of endoprosthesis assembly 1600. Optional pressure sensor 518 may be in communication with an external telemetry monitoring system (not shown) via a wireless communication system (not shown). Optional pressure sensor 518 may be used to indicate whether or not a successful deployment of endoprosthesis assembly 1600 has been achieved, and may also be used to monitor the patient's aneurysm by measuring the pressure therein.

Pressure sensor 518 may monitor the interior pressure of aneurysmic sac 521 by measuring the local pressure outside of endoprosthesis 1602 and inside the outstretched wall of aneurysmic sac 521. This would be of tremendous clinical value as the physician can monitor the status of aneurysmic sac 521 and adapt treatment according to aneurysmic behavior. Such a pressure sensor 518 would also have the benefit of measuring pressure during suction, so to avoid potential local negative pressures, and during injection of a substance, so to avoid excessive local pressures. In addition, pressure sensor 518 would also allow for the detection of potential endoleak, as if, for example, the sac is vacated and pressure is zero, an increase in pressure would indicate endoleak if no other parameters have changed. Furthermore, the pressure due to potential endoleak could also allow a physician, for example, to determine the desired substance/polymer pressure to counteract or oppose endoleak.

Figure 17:
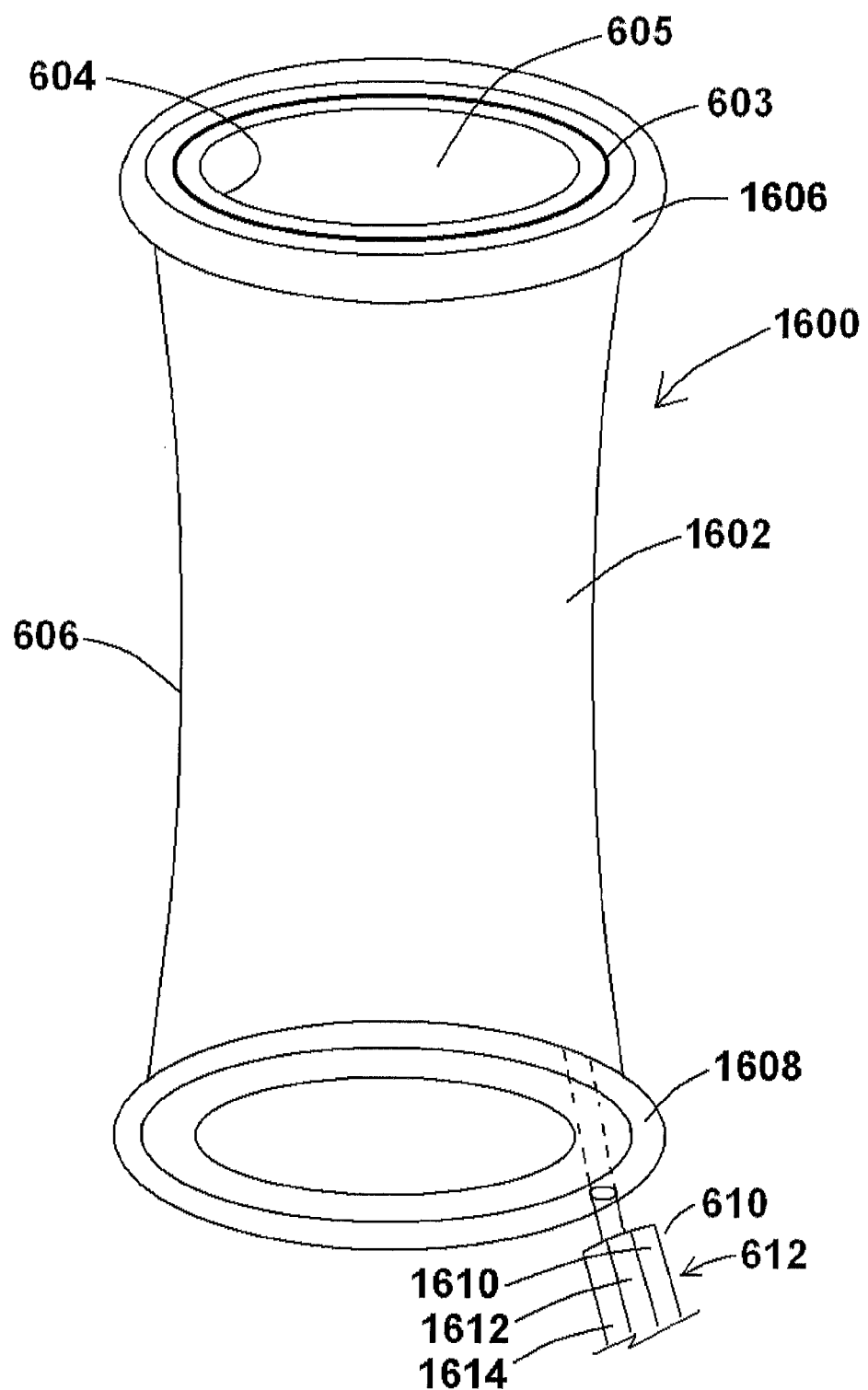

An additional embodiment of an endoprosthesis assembly 1600 of the present disclosure is shown in FIG. 17. As shown in FIG. 17, catheter 612 may couple directly to outer wall 606, or may indirectly couple to outer wall 606 by way of one or more connectors (as described in further detail herein) or other components so that suction from a suction/infusion source coupled to catheter 612 can cause local suction through the porous outer wall 606, and infusion from the suction/infusion source can deliver a substance through the porous outer wall 606 into a space within a luminal organ adjacent to outer wall 606. Such an embodiment of an endoprosthesis assembly 1600 as shown in FIG. 17 may have features of an endograft assembly 600 of the present disclosure, namely the absence of tube(s) 515 and/or 1604.

Figure 18A:
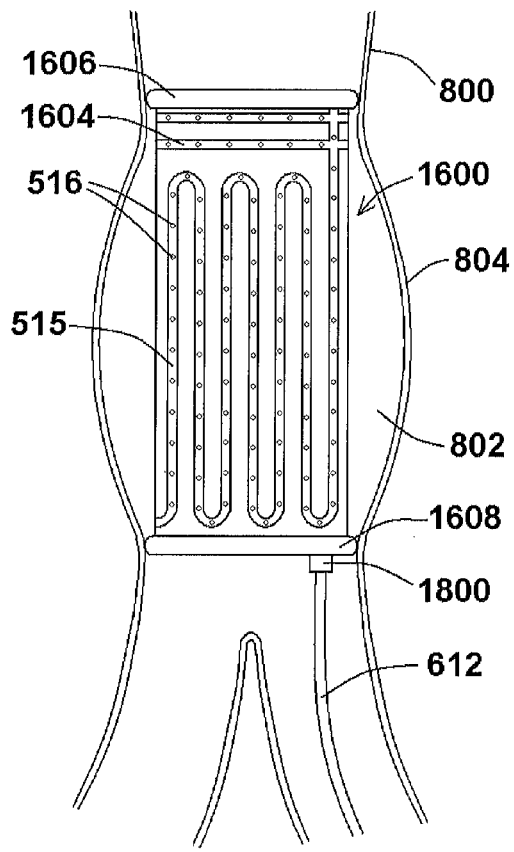
FIGS. 18A-18D show views of endoprosthesis assemblies according to exemplary embodiments of the present disclosure positioned within a luminal organ.
Figure 18B:
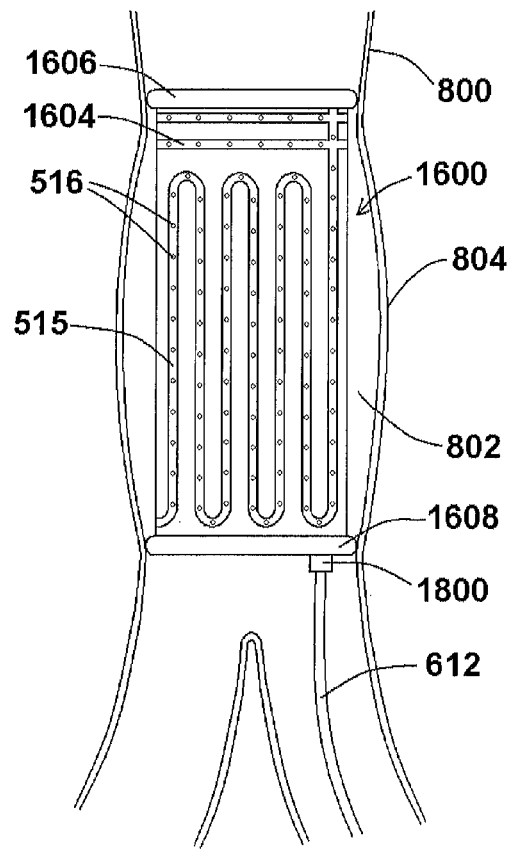
Figure 18C:
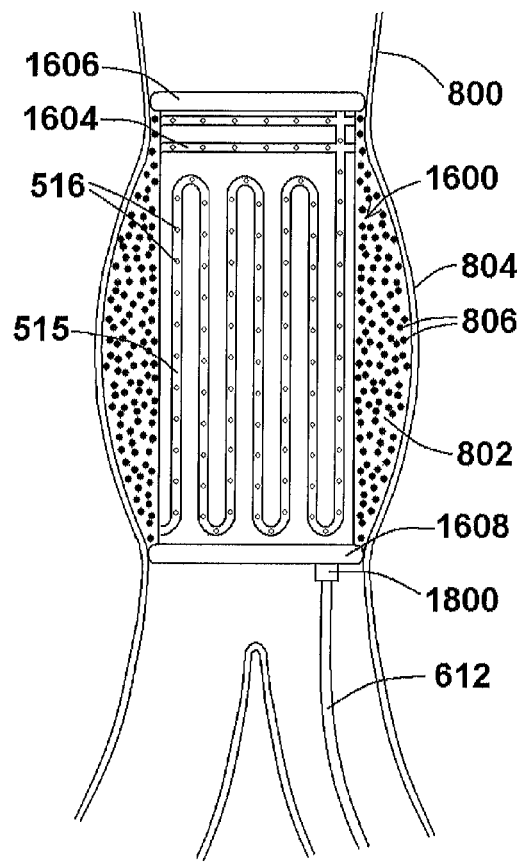

In at least one embodiment, and as shown in FIGS. 18A-18C, endoprosthesis assembly 1600 is configured to obviate the need for an endograft/endoprosthesis neck and hence the necessity for a good landing zone. This is because balloons 1606 and 1608 can be inflated when endoprosthesis assembly 1600 is positioned within a vessel at or near an aneurysm, whereby the inflation not only secures endoprosthesis assembly 1600 within the vessel, but also to prevent endoleak and/or leakage of casting material past the boundaries of endoprosthesis assembly 1600 so that the casting material does not leak into other areas of the patient's vascular system.

In addition, and as shown in FIG. 18A, various endoprosthesis assemblies 1600 of the present disclosure may comprise a valve mechanism 1800 to facilitate coupling of removable catheter 612 to endoprosthesis assembly 1600. Valve mechanism 1800 or removable catheter 612 may have one or more components as shown in FIGS. 9A-9C to facilitate coupling of removable catheter to a portion of endoprosthesis assembly 1600, such as balloon 1606, balloon 1608, first tube 515, second tube 516, outer wall 606, and the like. In at least one embodiment, valve mechanism 1800 comprises a valve so that when a removable catheter 612 is coupled thereto, fluid and/or a substance can pass in either direction through the valve, and when removable catheter 612 is not coupled thereto, fluid and/or a substance does not pass therethrough. In at least one embodiment, valve mechanism 1800 is a component of removable catheter 612, and in another embodiment, valve mechanism is coupled to a portion of endoprosthesis assembly 1600. In an embodiment when valve mechanism 1800 is not coupled to endoprosthesis assembly 1600, removal of catheter 612 effectively closes off the internal tubing/connectors within endoprosthesis assembly 1600. In at least one use of such an endoprosthesis assembly 1600, removable catheter 612 is coupled to endoprosthesis assembly 1600 at the level of the femoral artery where the endoprosthesis assembly 1600 is used in the case of an aortic abdominal aneurysm (AAA).

Figure 19:
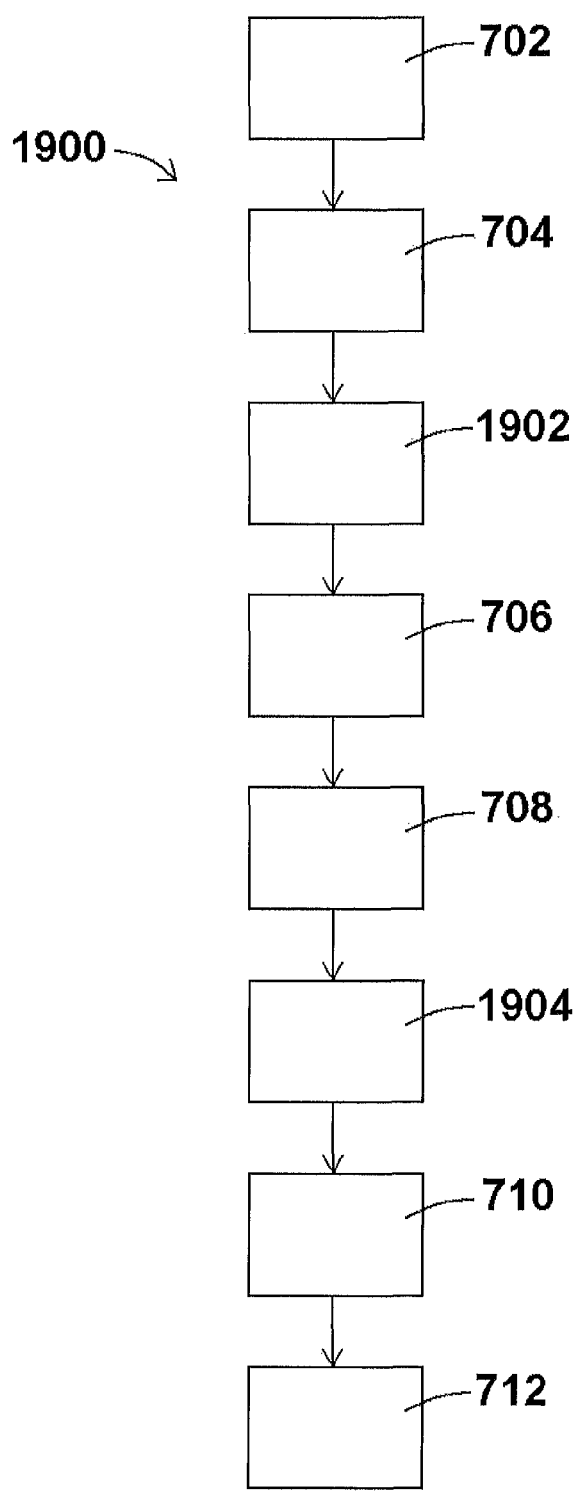
FIG. 19 shows a diagram of method steps of a method for using an endoprosthesis assembly according to an exemplary embodiment of the present disclosure.

Exemplary embodiments of endoprosthesis assemblies 1600 of the present disclosure may be used by performing the following method. Steps of an exemplary method 1900 for deploying and using an endoprosthesis assembly 1600 of the present disclosure are shown in FIG. 19. As shown in FIG. 19, method 1900 may comprise the step of delivering an endoprosthesis assembly 1600 to a desired site within a body, including, but not limited to, an aneurysm sac (an exemplary delivery step 702). This step may be performed using any number of methods for delivering endografts, endoprostheses, stents, and/or other implantable devices within a human body, so long as removable catheter 612 either remains affixed to tube(s) 515, 1604 (or another component of endoprosthesis assembly 1600) or is ultimately connected to tube(s) 515, 1604 (or another component of endoprosthesis assembly 1600), so that a suction/infusion source coupled to removable catheter 612 may be used as referenced herein. After endoprosthesis assembly 1600 is positioned within a vessel, graft portion 603 of endoprosthesis assembly 1600 may be opened/deployed from a closed/collapsed configuration (an exemplary deployment step 704) to secure endoprosthesis assembly 1600 within said vessel.

After endoprosthesis assembly 1600 has been deployed within the vessel, distal balloon 1606 and proximal balloon 1608 may be inflated using an inflation source coupled to removable catheter 612 (an exemplary balloon inflation step 1902). Performance of balloon inflation step 1902 not only helps to position/secure endoprosthesis assembly 1600 within the vessel, but also to isolate the aneurysm sac. As shown in FIG. 18A, endoprosthesis assembly 1600 has been delivered (by performing an exemplary delivery step 702), deployed (by performing an exemplary deployment step 704), and balloons 1606, 1608 have been inflated (by performing an exemplary balloon inflation step 1902) to secure endoprosthesis assembly 1600 in place.

After endoprosthesis assembly 1600 is deployed within the vessel and balloon inflation step 1902 has been performed, suction from a suction/infusion source may be used (an exemplary suction step 706) to withdraw, for example, blood, blood clots, and/or other particulates from an aneurysm sac, by way of blood and/or other materials entering tube openings 516 of tube 515 and/or tube 1604 present within/about endoprosthesis assembly 1600 (in an embodiment having tube(s) 515, 1604), or by way of blood and/or other materials entering outer wall 606 (in an embodiment not having tube(s) 515, 1604). Performance of suction step 706 may also cause the walls 804 of aneurysm sac 802 to collapse about endograft assembly 600, as shown in FIG. 18B. The degree to which said walls 804 may collapse about endoprosthesis assembly 600 depends on the relative thickness of said sac/vessel walls and/or the relative suction pressure used. In at least one embodiment, suction (to reduce overall blood/clot volume within the aneurysm) can be measured to ensure near zero aneurysm pressure should such a level be desired.

Figure 18D:
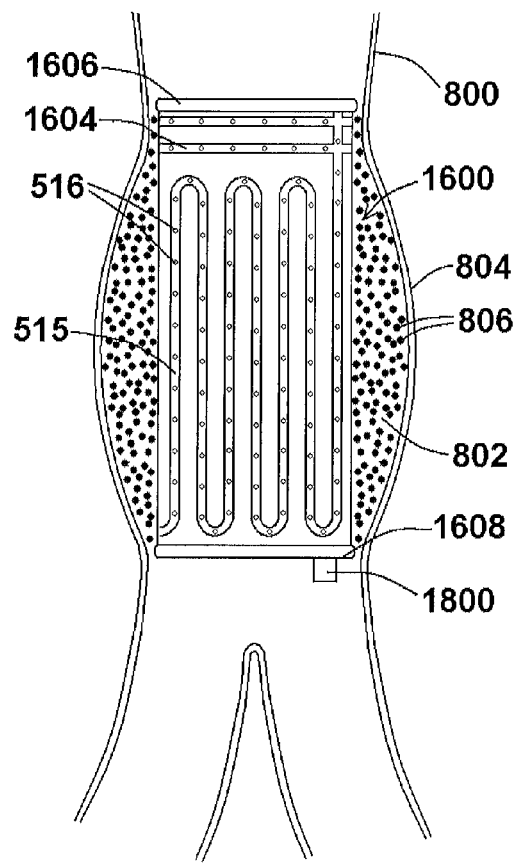

After removal of fluid from the area of interest, suction/infusion source 614 may be used to inject a substance (an exemplary injection step 708) into, for example, the aneurysm sac. Such a substance may comprise any number of biocompatible liquids including, but not limited to, various polymers such as ethylene vinyl alcohol (EVOH) copolymer, acetate polymer, EVOH dissolved in dimethyl sulfoxide (DMSO), cellulose, cyanoacrylates, various glues, and gel magnetic polymer. Injection of such substances into the aneurysm sac would be performed to strengthen/reinforce the weakened aneurysm sac walls (forming a rigid or semi-flexible cast) to reduce the likelihood of or prevent aneurysm rupture, which can be fatal in many instances. Said substances may also prevent the migration of an endoprosthesis assembly 1600 within the vessel by adhering to said assembly 1600. Injection step 708 may be performed by injecting the substance through openings 516 of tube(s) 515, 1604 (in embodiments of endoprosthesis assemblies having tube(s) 515, 1604), or may be performed by injecting the substance through outer wall 606 (in embodiments not having tube(s) 515, 1604), as shown in FIG. 18C. Injection of a substance through tube 1604, when tube 1604 is in a circumferential/ring configuration at or near the distal end of endoprosthesis 1602, can cause more substance to be injected locally at or near the distal end (also as shown in FIG. 18C), further enhancing and/or improving the overall casting of the substance to encourage a viable cast and also to potentially prevent spreading of the aneurysm itself. FIGS. 18C and 18D depict this procedure, with the black dots representing injected substance 806. In at least one embodiment, injection step 708 is performed using injection pressure maintained at or near 30 mmHg or less, and the infused volume of substance is between approximately 50 and 80 mL.

After all suction and injection steps have been performed, balloons 1606, 1608 can be deflated if desired (an optional exemplary balloon deflation step 1904), as shown in FIG. 18D, and removable catheter 612 would be disconnected from tube 515 or another portion of endoprosthesis assembly 1600 (an exemplary catheter disconnection step 710) so that the endoprosthesis assembly 1600 would be separate from removable catheter 612. Removable catheter 612 may then be withdrawn from the patient's body (an exemplary catheter withdrawal step 712), also as shown in FIG. 18D, allowing the endoprosthesis assembly 1600, with substance 806 (as shown in FIGS. 18C and 18D, for example) positioned external to assembly 1600 to reinforce weakened aneurysm sac walls, to remain within the body. Balloon deflation step 1904, in at least one embodiment, may be performed within a few minutes of performing injection step 708, as substances 806 would "cure" relatively quickly. Disconnection step 710, in at least one embodiment, causes the valve within valve mechanism 1800 to close to isolate the connection between the internal components/tubes of endoprosthesis assembly 1600 from the patient's blood circulation, Several advantages and indications exist for such an aforementioned endoprosthesis assembly 1600 (which may be referred to herein as a "single self-supporting endoprosthesis" given that only one is used at a particular area). Exemplary indications are for chronic cases with regular size of iliac or femoral arteries to allow the use of regular introducer sizes. Exemplary embodiments of endoprosthesis assemblies 1600 allow for relatively fast insertion and localization of the landing zone since it is not important to have a "good" landing zone or neck as with current endografts. In addition, various embodiments can be used to effectively isolate a rupture or bleeding of the aneurysm (such as an AAA), and the solid cast ensures that the blood pressure cannot transmit to the aneurysm wall to prevent rupture. The aneurysm cast may also anchor the endoprosthesis assembly 1600 at the level of the aneurysm neck to eliminate migration.

Furthermore, and with respect to the foregoing, Endoleak type I is eliminated because the flow through the neck cannot be transmitted through the wall of the aneurysm sac due to the solid cast. Similarly, Endoleak type II is prevented because the cast physically blocks the source arteries branches for endoleak II. In addition, the cast can be made at pressure of about 30 mmHg, which is equal to or greater than the pressure of the endoleak arteries. Finally, the aneurysm cast supports the endoprosthesis assembly 1600 material and can prevent Endoleak III which typically occurs from fatigue of a typical endoprosthesis. Furthermore, such an exemplary method 1900 does not use barbs or hooks to support the endoprosthesis assembly 1600 at the level of the landing zone, thereby avoiding aortic wall lesions. The self supporting endoprosthesis assembly 1600 (balloon+aneurysm neck cast+aneurysm sac cast) avoid the need for current mechanical support mechanisms.

Figure 20A:
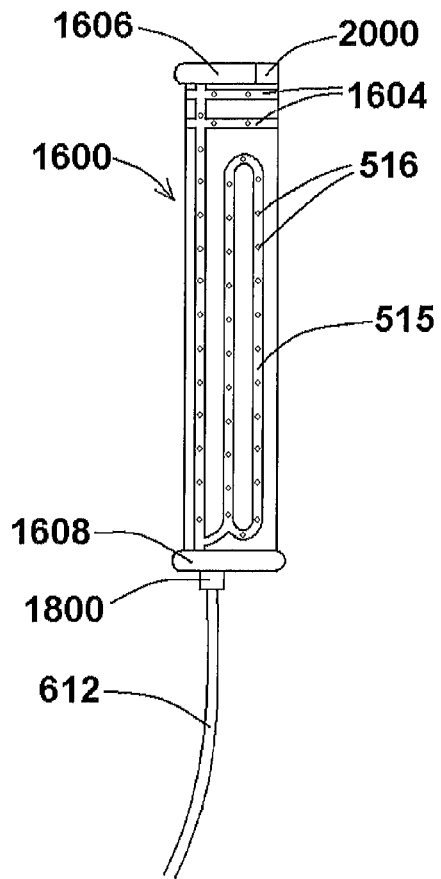
FIGS. 20A and 20B show front views of endoprosthesis assemblies according to exemplary embodiments of the present disclosure.
Figure 20B:
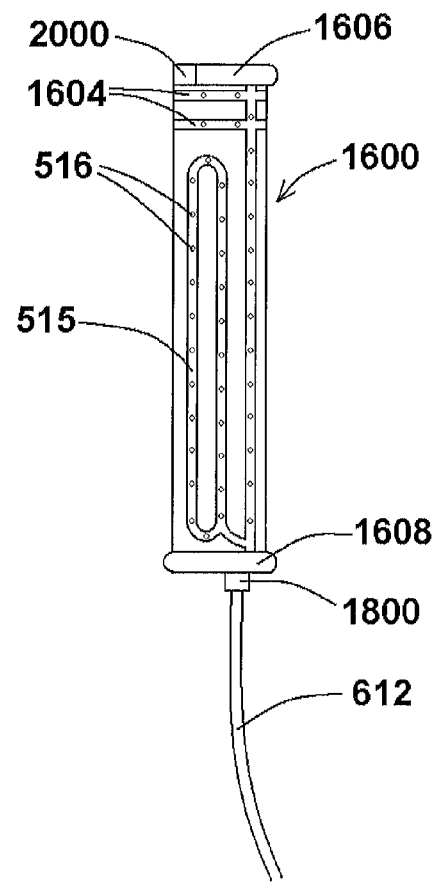

Additional exemplary embodiments of endoprosthesis assemblies 1600 of the present disclosure are shown in FIGS. 20A and 20B. As shown in FIGS. 20A and 20B, endoprosthesis assemblies 1600 comprise a number of features as shown and described in connection with other embodiments, such as distal balloon 1606, proximal balloon 1608, tubes 515, 1604 defining tube openings 516, and a valve mechanism 1800. Other features of other embodiments of endoprosthesis assemblies 1600 of the present disclosure may also be present within the embodiments shown in FIGS. 20A and 20B.

Figure 21:
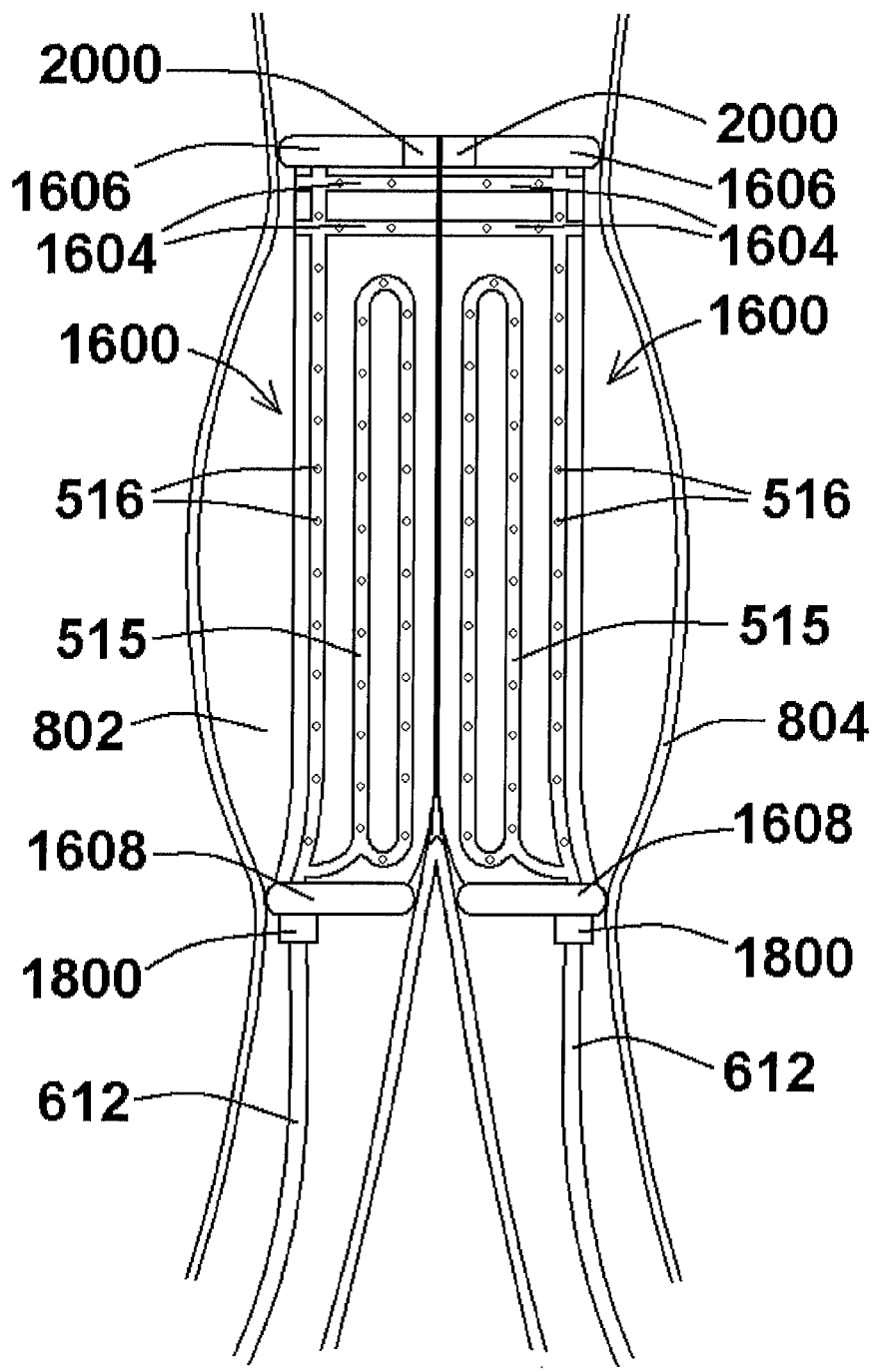
FIG. 21 shows endoprosthesis assemblies according to exemplary embodiments of the present disclosure positioned within a luminal organ.

In addition, exemplary embodiments of endoprosthesis assemblies 1600 of the present disclosure may comprise one or more magnetic mechanisms 2000, which may include one or more magnets that attract one another, or one or more magnets on one endoprosthesis assembly 1600 that attracts one or more metal components present on another adjacent endoprosthesis assembly 1600. Furthermore, and as shown in FIGS. 20A and 20B, one or both of balloons 1606, 1608 may not be completely circumferential, as balloons 1606, 1608 extending less than 360° (such as, for example, about 180°, about 270°, or some other amount greater than about 180° but less than about 360°) may be desired so that when two endoprosthesis assemblies 1600 are positioned adjacent to one another and balloons 1606, 1608 are inflated, inflation of balloons 1606, 1608 does not cause the two embodiments to separate from one another. As shown in FIG. 21, for example, balloons 1606 would be less than 360° around endoprosthesis assembly 16000, and balloons 1608 would remain at 360° around endoprosthesis assembly 1600 given their relative positioning within the bifurcated vessel.

As shown in FIGS. 20A and 20B, tubes 515 are arranged so that when both embodiments of endoprosthesis assemblies 1600 are positioned within a luminal organ and a substance is injected therethrough to form a cast, the amount of substance that is injected between the two endoprosthesis assemblies 1600 is either significantly minimized or eliminated. It may be desired to have some substance injected between the two embodiments (to help secure them together), but in various methods/uses, it may be desired not to have any substance injected between the two embodiments as such an injection may have the effect of separating the two embodiments from one another.

FIG. 21 shows two exemplary embodiments of endoprosthesis assemblies 1600 of the present disclosure positioned within a bifurcated vessel, such as near an AAA. As shown therein, a first endoprosthesis assembly 1600 is positioned on a relative left side of the vessel, and a second endoprosthesis assembly 1600 is positioned on a relative right side of the vessel. The proximal portions of each assembly 1600, as shown in the figure, may be positioned within separate bifurcations, so that inflation of proximal balloons 1608 of each assembly 1600 cause the assemblies to engage the bifurcations so that when the distal balloons 1606 are also inflated and a substance is injected through assemblies 1600 to form a cast, part of the cast will be in each part of the bifurcated vessel.

Several advantages and indications exist for such endoprosthesis assemblies 1600 (each of which may be referred to herein as a "double self-supporting endoprosthesis" given that two are used at a particular area). Two or more endoprosthesis assemblies 1600 of the present disclosure, or one or more endoprosthesis assemblies 1600 and various additional components of the present disclosure may also be referred to herein as an "endoprosthesis system." As shown in FIG. 21, magnetic mechanisms 2000 of each embodiment attract one another, allowing for the two assemblies to align and position relative to one another, and potentially also to provide an element to be visualized using x-ray or another visualization method. Each assembly 1600, as shown in FIG. 21, would be inserted (potentially simultaneously) using two different punctures, such as femoral or iliac punctures, wherein the assemblies shown in FIGS. 18A-18D would be inserted using a single puncture. Such embodiments could be used for AAA sac rupture or for small femoral or iliac artery sizes allowing the use of a smaller introducer. Relatively fast insertion could be performed without the need for a good landing zone in an emergency case of sac rupture given the presence of balloons 1606, 1608 about each assembly 1600, to effectively isolate rupture and/or bleeding of the aneurysm. Other advantages of other embodiments of endoprosthesis assemblies 1600 of the present disclosure may also apply to the double self-supporting embodiments referenced herein.

A method of using such an embodiment of a double self-supporting endoprosthesis could minor method 1900, noting that two endoprosthesis assemblies 1600 would be inserted, and an additional step of aligning the endoprosthesis assemblies 1600 using the magnetic mechanisms would also take place. For example, and as shown in the method 1900 embodiment shown in FIG. 19, an exemplary delivery step 702 would comprise the delivery of two endoprosthesis assemblies 1600 potentially using two separate punctures, and an exemplary deployment step 704 would include deployment of both assemblies 1600. Delivery step 702 could also comprise alignment of the endoprosthesis assemblies relative to one another by way of positioning magnetic mechanisms 2000 of adjacent endoprosthesis assemblies 1600 relative to one another. One or more remaining steps of method 1900 would be repeated for each assembly 1600 used, for example.

Figure 22:
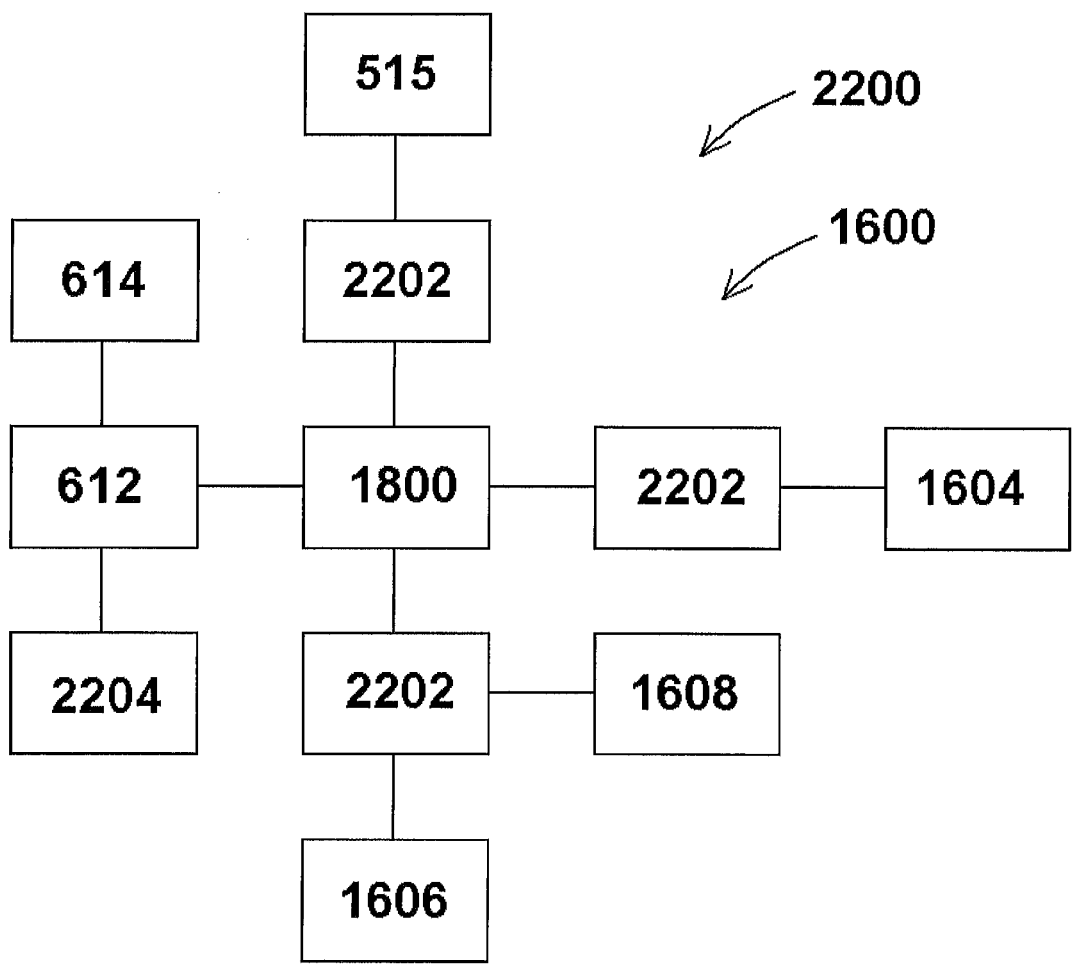
FIG. 22 shows a block diagram of various components of an exemplary embodiment of an endoprosthesis assembly of the present disclosure.

FIG. 22 shows a block diagram of various components of exemplary endoprosthesis assemblies 1600 (or endoprosthesis systems 2200) of the present disclosure. As shown in FIG. 22, one exemplary embodiment of an endoprosthesis assembly 1600 of the present disclosure comprises a valve mechanism 1800 configured to receive part of catheter 612, and as shown therein, various connectors 2202, such as tubes, for example, are used to couple valve mechanism 1800 to one or more of tubes 515, 1604 and/or balloons 1606, 1608. Catheter 612, as shown therein, may also be coupled to one or more of a suction/infusion source 614 and an inflation/deflation source 2204. The block diagram shown in FIG. 22 is not intended to represent all embodiments of the present disclosure, as various endoprosthesis assemblies 1600 and/or endoprosthesis systems 2200 of the present disclosure may include more, fewer, or no connectors 2202, or may include connectors 2202 configured differently than as shown therein. In addition, various endoprosthesis assemblies 1600 and endoprosthesis systems 2200 may comprise any number of other components referenced herein, such as an endoprosthesis 602, a structure 603, an inner wall 604, an outer wall 606, tube(s) 515, 1604, balloon(s) 1606, 1608, a valve mechanism 1800, and/or the like.

Figure 23:
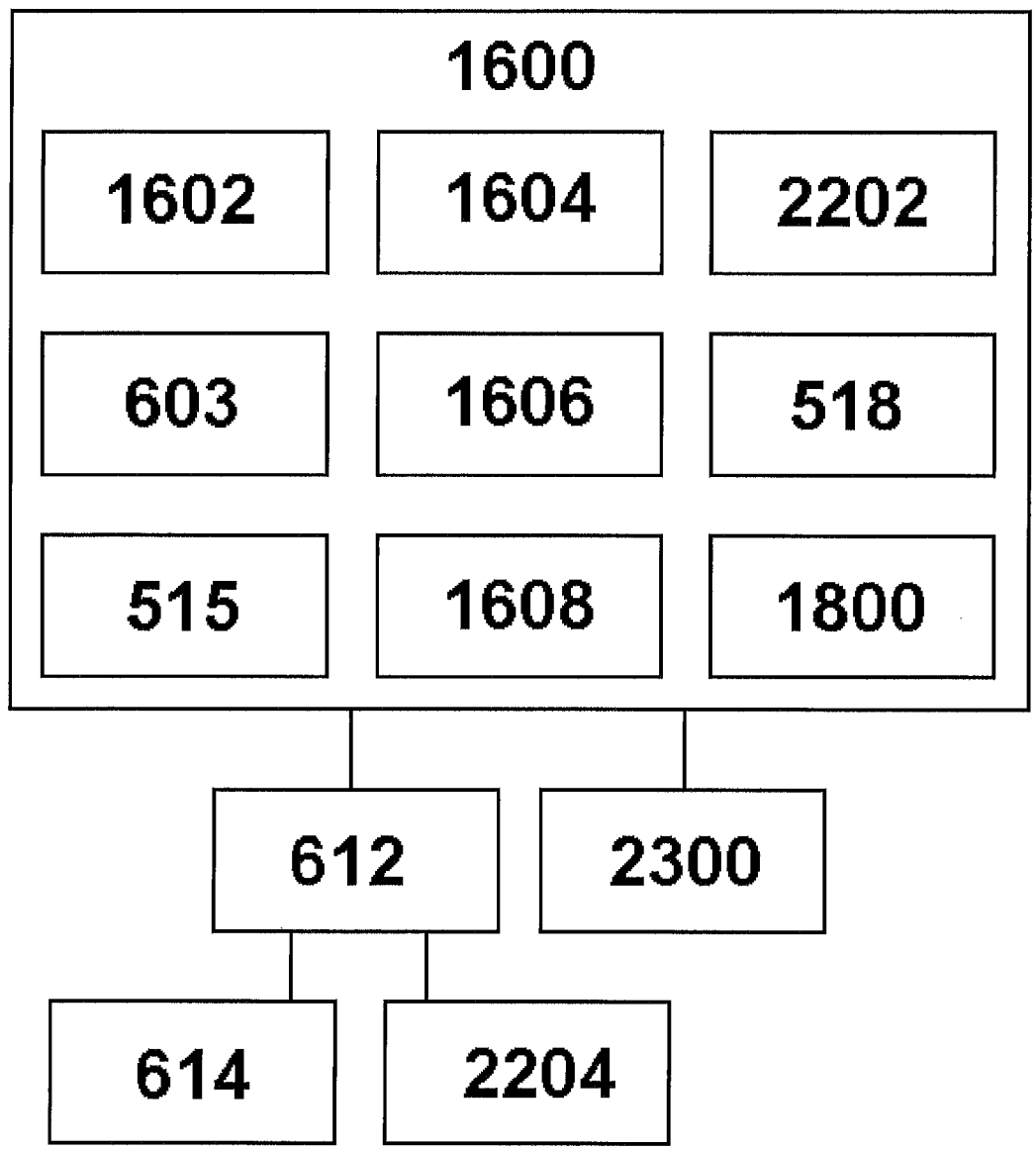
FIG. 23 shows another block diagram of various components of an exemplary embodiment of an endoprosthesis assembly of the present disclosure.

In addition, and to visually depict various components of an exemplary endoprosthesis assembly 1600 of the present disclosure, FIG. 23 shows a block diagram of an exemplary endoprosthesis assembly 1600 comprising an endoprosthesis 1602, an additional structure 603, tubes 515, 104, balloons 1606, 1608, a pressure sensor 518, and a valve mechanism 1800. In addition, an exemplary endoprosthesis assembly would be configured to receive a portion of a removable catheter 612, and would also be in communication with, for example, a suction/infusion source 614, an inflation/deflation source 2204, and a telemetry monitor 2300 to measure/obtain pressure measurements from pressure sensor 518.

Several advantages to exemplary endograft assemblies 600, endoprosthesis assemblies 1600, and/or endoprosthesis systems 2200 of the present disclosure also include the following. First, the collapsible sponge sheath 1000 of endograft assembly 600, positioned closely to the external surface of endograft 602, may vary its volume according to the size of its pores and may occupy some or all of the aneurysm sac cavity. The pores within sponge sheath 1000 may facilitate the removal of blood content from the aneurysm sac cavity to enter sponge sheath 1000, thus collapsing the aneurysm sac wall about endograft assembly 600. The combination of sponge sheath 1000 (with its inherent pores) and sponge channels 1002 allow relatively easy removal of blood from the aneurysm sac and the injection of substances into the aneurysm sac with low resistance. Furthermore, the collapsible sponge sheath 1000 may be useful for all EVAR endoprosthesis procedures in order to form a cast around the endograft assembly 600, filling the aneurysm sac, and avoiding many complications such as migration, endoleak, and structural alterations of endograft 602 produced by the stress-stretching pressure wall effect.

The various endograft assemblies 600, endoprosthesis assemblies 1600, and/or endoprosthesis systems 2200 of the present disclosure, as well as components coupled thereto, may comprise any number of suitable medical grade materials, including, but not limited to, nitinol, various plastics, polyurethane, silastic, polyvinylchloride (PVC), and polytetrafluoroethylene (PTFE).

As shown in the various embodiments of endograft assemblies 600, endoprosthesis assemblies 1600, and endoprosthesis systems 2200 of the present disclosure, said assemblies 600, 1600 are configured to permit blood flow through the vessel for which they are placed. Said assemblies 600, 1600 and systems 2200 also have the additional advantage of being used in all EVAR endoprosthesis procedures in order to perform a cast around assemblies 600, 1600, filling the aneurysm sac and avoiding several complications such as Endoleak I and II and structural alterations of the endograft assembly 600 produced by the stress stretching pressure wall effect.

Endograft assemblies 600 and endoprosthesis assemblies 1600 of the present disclosure may be delivered and/or positioned within a vessel lumen using any number of medical tools known in the art to deliver stents and/or endografts.

Although the above exemplary embodiments of the present disclosure are described in connection with treatment of aneurysms, including an abdominal aortic aneurysm, the disclosure of the present application is not limited to its use in correcting aneurysms. Many other uses are possible within the scope of the present disclosure. For example, the combination of a metallic material and a corresponding magnetic device may be used for the correction of the structure or architecture of organs, such as the heart or along other parts of the aorta or other vessels.

While various embodiments of devices and methods for treating aneurysms have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An endoprosthesis assembly, comprising:
   an endoprosthesis having an impermeable inner wall;
   a first balloon at or near a distal end of the endoprosthesis and a second balloon at or near the proximal end of the prosthesis; and
   a first tube defining one or more tube openings positioned on a relative outside of the inner wall, the one or more tube openings are exposed along a relative outside of the endoprosthesis assembly;
   wherein the endoprosthesis assembly is configured to isolate an aneurysm sac of a luminal organ when positioned therein.

2. The endoprosthesis assembly of claim 1, wherein the endoprosthesis further comprises a permeable outer wall adjacent to the impermeable inner wall.

3. The endoprosthesis assembly of claim 2, wherein the permeable outer wall is configured so that fluid can flow through the permeable outer wall due to its permeability.

4. The endoprosthesis assembly of claim 2, wherein the first tube is positioned within the permeable outer wall.

5. The endoprosthesis assembly of claim 2, further comprising:
   a second tube defining one or more second tube openings positioned at or within the outer wall of the endoprosthesis.

6. The endoprosthesis assembly of claim 1, wherein the one or more tube openings are exposed along the relative outside of the inner wall.

7. The endoprosthesis assembly of claim 1, wherein when the endoprosthesis assembly is positioned within the luminal organ at the aneurysm sac, inflation of the first balloon and the second balloon effectively isolates the aneurysm sac and prevents fluid present within the aneurysm sac from flowing past the first balloon and the second balloon.

8. The endoprosthesis assembly of claim 1, further comprising:
   a graft structure positioned adjacent to the inner wall of the endoprosthesis, the graft structure capable of expansion to expand the endoprosthesis.

9. The endoprosthesis assembly of claim 1, further comprising:
   a catheter having a distal catheter end, a proximal catheter end, and defining a suction/infusion lumen therethrough and an inflation/deflation lumen therethrough, wherein the distal catheter end of the catheter is configured to be removably coupled to the endoprosthesis at or near the proximal end of the endoprosthesis.

10. The endoprosthesis assembly of claim 9, further comprising:
    a suction/infusion source configured to be coupled to the catheter at or near the proximal catheter end, the suction/infusion source capable of providing suction within the suction/infusion lumen of the catheter to facilitate removal of blood present within the aneurysm sac and further capable of injecting a substance into the suction/infusion lumen of the catheter so to form a cast within the aneurysm sac.

11. The endoprosthesis assembly of claim 1, further comprising:
    a valve mechanism coupled to the endoprosthesis, the valve mechanism configured to receive a distal catheter end of a catheter, the valve mechanism further configured to permit fluid to flow in and out of the valve mechanism when the catheter is coupled thereto, the valve mechanism further configured to prevent fluid from flowing in and out of the valve mechanism when the catheter is not coupled thereto.

12. The endoprosthesis assembly of claim 1, further comprising:
    a magnetic mechanism coupled to the endoprosthesis assembly at or near the distal end of the endoprosthesis, the magnetic mechanism configured to attract a second magnetic mechanism of a second endoprosthesis assembly positioned relative to the endoprosthesis assembly.

13. The endoprosthesis assembly of claim 1, further comprising:
    a pressure sensor coupled thereto, the pressure sensor operable to obtain at least one pressure measurement of an environment surrounding the endoprosthesis.

14. An endoprosthesis assembly, comprising:
    an endoprosthesis having an impermeable inner wall;
    a first balloon at or near a distal end of the endoprosthesis and a second balloon at or near the proximal end of the prosthesis; and
    a first tube defining one or more tube openings positioned on a relative outside of the inner wall, the one or more tube openings are exposed along a relative outside of the endoprosthesis assembly;
    wherein the endoprosthesis assembly is configured to isolate an aneurysm sac of a luminal organ when positioned therein and the first balloon and the second balloon are inflated, and wherein the endoprosthesis assembly is further configured to facilitate removal of blood present within the aneurysm sac using the one or more tube openings.

15. The endoprosthesis assembly of claim 14, further configured to introduce a cast substance into the aneurysm sac using the one or more tube openings or one or more second tube openings of a second tube positioned on the relative outside of the inner wall.

16. The endoprosthesis assembly of claim 14, wherein the impermeable inner wall defines a lumen therethrough, and wherein when the endoprosthesis assembly is positioned within the luminal organ, blood may flow through the luminal organ through the lumen.

17. A method for using an endoprosthesis assembly, the method comprising the steps of:
    delivering an endoprosthesis assembly within a vessel of a patient at or near the site of an aneurysm sac of a vessel aneurysm, the endoprosthesis assembly comprising:
       an endoprosthesis having an impermeable inner wall;
       a first balloon at or near a distal end of the endoprosthesis and a second balloon at or near the proximal end of the prosthesis;
       a first tube defining one or more tube openings positioned on a relative outside of the inner wall, the one or more tube openings are exposed along a relative outside of the endoprosthesis assembly; and
       a catheter having a distal catheter end, a proximal catheter end, and defining a first catheter lumen and a second catheter lumen therethrough, wherein the distal catheter end of the catheter is configured to be removably coupled to the endoprosthesis; and
    operating an inflation/deflation source in communication with the first catheter lumen to inflate the distal balloon and the proximal balloon to isolate the aneurysm sac and prevent fluid within the aneurysm sac from flowing past the distal balloon and the proximal balloon.

18. The method of claim 17, further comprising the steps of:
operating a first suction/infusion source in communication with the second catheter lumen to remove blood present within the aneurysm sac; and
operating the suction/infusion source or a second suction/infusion source to inject a substance into the aneurysm sac to form a cast at or near the vessel aneurysm.

19. The method of claim 18, wherein the step of operating the first suction/infusion source to remove blood present within the aneurysm sac causes a wall of the aneurysm to collapse toward the endoprosthesis assembly.

20. The method of claim 18, wherein the step of operating first suction/infusion source to remove blood is performed along with a step of obtaining a first pressure measurement using a pressure sensor in communication with the aneurysm sac so to avoid negative pressure within the aneurysm sac, and wherein the step of operating the first suction/infusion source or the second suction/infusion source to inject a substance is performed along with a step of obtaining a second pressure measurement using the pressure sensor so to avoid excessive pressure within the aneurysm sac.

* * * * *